US012642764B2

(12) United States Patent
Jang et al.

(10) Patent No.: US 12,642,764 B2
(45) Date of Patent: Jun. 2, 2026

(54) FUSION PROTEIN PREPARATION COMPRISING IL-2 AND CD80 PROTEINS

(71) Applicant: GI INNOVATION, INC., Seoul (KR)

(72) Inventors: Myung Ho Jang, Seoul (KR); Young Min Oh, Yongin-si (KR); Heonchang Lim, Incheon (KR)

(73) Assignee: GI INNOVATION, INC., Seoul (KR)

( * ) Notice: Subject to any disclaimer, the term of this patent is extended or adjusted under 35 U.S.C. 154(b) by 930 days.

(21) Appl. No.: 17/912,398

(22) PCT Filed: Mar. 17, 2021

(86) PCT No.: PCT/KR2021/003312
§ 371 (c)(1),
(2) Date: Sep. 16, 2022

(87) PCT Pub. No.: WO2021/187897
PCT Pub. Date: Sep. 23, 2021

(65) Prior Publication Data
US 2023/0125871 A1     Apr. 27, 2023

(30) Foreign Application Priority Data
Mar. 18, 2020     (KR) ........................ 10-2020-0033231

(51) Int. Cl.
| | |
|---|---|
| *A61K 38/17* | (2006.01) |
| *A61K 9/08* | (2006.01) |
| *A61K 38/20* | (2006.01) |
| *A61K 47/10* | (2017.01) |
| *A61K 47/18* | (2017.01) |
| *A61K 47/22* | (2006.01) |
| *A61K 47/26* | (2006.01) |

(52) U.S. Cl.
CPC ............ *A61K 9/08* (2013.01); *A61K 38/1774* (2013.01); *A61K 38/2013* (2013.01); *A61K 47/10* (2013.01); *A61K 47/183* (2013.01); *A61K 47/22* (2013.01); *A61K 47/26* (2013.01)

(58) Field of Classification Search
CPC ........................ A61K 38/1774; A61K 38/2013
See application file for complete search history.

(56) References Cited

U.S. PATENT DOCUMENTS 5,955,427 A     9/1999   Mcgregor et al.

FOREIGN PATENT DOCUMENTS

| | | |
|---|---|---|
| CN | 105816858 A | 8/2016 |
| CN | 110709062 A | 1/2020 |
| JP | 10-513433 A | 12/1998 |
| JP | 2011-508742 A | 3/2011 |
| KR | 10-1643277 B1 | 7/2016 |
| KR | 10-2201086 B1 | 1/2021 |
| WO | 2009/086296 A2 | 7/2009 |
| WO | 2009/086400 A2 | 7/2009 |
| WO | 2017/078385 A1 | 5/2017 |
| WO | 2018/187057 A1 | 10/2018 |
| WO | 2020/060122 A1 | 3/2020 |

OTHER PUBLICATIONS

Bork. Powers and Pitfalls in Sequence Analysis: The 70% Hurdle. Genome Research, 2000, 10:398-400 (Year: 2000).*
Greenspan et al. 1999. Defining epitopes: It's not as easy as it seems; Nature Biotechnology, 17:936-937 (Year: 1999).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine ResidueJ. Cell Biol. 111:2129-2138, 1990 (Year: 1990).*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Linghong Kong, et al., "Expression of fusion IL2-B7.1(IgV+C) and effects on T lymphocytes", Biochem. Cell Biol., 2007, vol. 85, 685-695 (11 pages).
J.C. Park et al., " GI101, a novel triple-targeting bispecific CD80-IgG4-IL2variant fusion protein, elicits synergistic anti-tumour effects in preclinical models", Immunotherapy of Cancer, Oct. 2019, 1 pg., vol. 30, No. 5.
Lucas Chan et al., "IL-2/B7.1 (CD80) Fusagene Transduction of AML Blasts by a Self-Inactivating Lentiviral Vector Stimulates T Cell Responses in Vitro: a Strategy to Generate Whole Cell Vaccines for AML", Molecular Therapy, Jan. 2005, p. 120-131, vol. 11, No. 1.
Hisashi Imai et al., "Depletion of CD4+CD25+ regulatory T cells enhances interleukin-2-induced antitumor immunity in a mouse model of colon adenocarcinoma", Cancer Sci, Mar. 2007, pp. 416-423, vol. 98, No. 3.
International Search Report for PCT/KR2021/003312 dated, Jul. 12, 2021 (PCT/ISA/210).
Taiwanese Search Report for 110109829 dated Feb. 11, 2022.

* cited by examiner

*Primary Examiner* — Prema M Mertz
(74) *Attorney, Agent, or Firm* — Sughrue Mion, PLLC

(57) ABSTRACT

The present invention relates to a pharmaceutical formulation with enhanced stability of a fusion protein dimer comprising a modified IL-2 protein and a CD80 protein. The fusion protein dimer comprising an IL-2 protein and a CD80 protein can not only activate immune cells owing to IL-2, but also effectively regulate Treg cells owing to CD80. When the formulation according to the present invention is applied to a fusion protein dimer comprising an IL-2 protein and a CD80 protein, the stability of the fusion protein dimer is significantly increased, and it can be used as a liquid formulation. Accordingly, the commercial applicability of the fusion protein dimer can be increased.

23 Claims, 3 Drawing Sheets
Specification includes a Sequence Listing.

FUSION PROTEIN PREPARATION COMPRISING IL-2 AND CD80 PROTEINS

CROSS REFERENCE TO RELATED APPLICATIONS

This application is a National Stage of International Application No. PCT/KR2021/003312 filed Mar. 17, 2021, claiming priority based on Korean Patent Application No. 10-2020-0033231 filed Mar. 18, 2020.

INCORPORATION BY REFERENCE OF SEQUENCE LISTING

The content of the electronically submitted sequence listing, file name: Sequence_Listing_As_Filed.txt; size: 98,579 bytes; and date of creation: Sep. 16, 2022, filed herewith, is incorporated herein by reference in its entirety.

TECHNICAL FIELD

The present invention relates to a liquid formulation with enhanced stability of a fusion protein comprising an IL-2 protein and a CD80 protein.

BACKGROUND ART

IL-2, also called T-cell growth factor, is a globular glycoprotein that plays a central role in lymphocyte production, survival, and homeostasis. IL-2 has a protein size of about 15.5 kDa to about 16 kDa and consists of 133 amino acids. IL-2 mediates various immune actions by binding to an IL-2 receptor composed of three distinct subunits. In addition, IL-2 is synthesized mainly by activated T cells, in particular by CD4+ helper T cells. IL-2 stimulates proliferation and differentiation of T cells, and induces production of cytotoxic T lymphocytes and differentiation of peripheral blood lymphocytes into cytotoxic cells and lymphokine-activated killer cells.

Furthermore, IL-2 is involved in proliferation and differentiation of B cells, and promotes immunoglobulin synthesis by B cells. In addition, IL-2 stimulates production, proliferation, and activation of natural killer cells. Therefore, IL-2 is used as an anticancer agent, because it can increase lymphocyte populations and increase the function of the immune cells in vivo. Currently, therapy with IL-2 has been approved for patients with metastatic renal cell carcinoma and malignant melanoma.

However, IL-2 has a dual function in that it is important not only for mediating an increase in number of immune cells and activity thereof, but also for maintaining immune tolerance. In addition, it has been reported that IL-2 may not be optimal for inhibiting tumor growth. The reason is that in the presence of IL-2, activation-induced cell death (AICD) may occur in the resulting cytotoxic T lymphocytes and immune responses may be inhibited by IL-2-dependent regulatory T cells (Treg cells) (Imai et al., *Cancer Sci* 98, 416-423, 2007).

In addition, severe cardiovascular, pulmonary, renal, hepatic, gastrointestinal, neuronal, dermatological, hematological, and systemic side effects occur in patients who have received IL-2. Therefore, various IL-2 mutants have been studied to improve therapeutic efficacy of IL-2 and minimize side effects thereof (U.S. Pat. No. 5,229,109 B). However, there are still many problems to be solved in order to utilize IL-2 for pharmacological purposes.

Meanwhile, CD80, also known as B7-1, is a member of the B7 family of membrane-bound proteins that are involved in immune regulation by binding to its ligand by way of delivering costimulatory responses and coinhibitory responses. CD80 is a transmembrane protein expressed on the surface of T cells, B cells, dendritic cells, and monocytes. CD80 is known to bind CD28, CTLA4 (CD152), and PD-L1. CD80, CD86, CTLA4, and CD28 are involved in a costimulatory-coinhibitory system. For example, CD80 is known to regulate activity of T cells and to be involved in proliferation, differentiation, and survival thereof.

For example, when CD80 and CD86 interact with CD28, costimulatory signals are generated to activate T cells. Eventually, CD80 binds to CTLA4 expressed on the surface of activated T cells and stimulates CTLA4 to be upregulated. As a result, CD80 inhibits T cell responses prior to immune response operation caused by CD80/CD28 interaction. This feedback loop allows for fine regulation of immune responses.

In addition, CD80 is known to bind PD-L1, another B7 family member, with affinity similar to that with which CD28 binds PD-L1. PD-L1 is known as one of two ligands for programmed death-1 (PD-1) protein, and PD-L1 is known to be involved in T cell regulation. Binding of CD80 to PD-L1 is another mechanism that can block PD-1/PD-L1 interaction, which may prevent inhibition of T cell responses in tumors. However, an increase in CD80 levels causes CD80 to bind to CD28, thereby inducing T cell responses. At the same time, CD80 may bind to CTLA4, thereby inhibiting T cell responses.

It was confirmed that a fusion protein comprising a CD80 fragment, an immunoglobulin Fc, and an IL-2 variant can activate immune cells, and at the same time, can control the immune cell regulatory activity of regulatory T cells, and thus can efficiently treat cancer as well as an infectious disease (KR 10-2201086 B1). In order to efficiently apply such protein to the treatment of cancer disease and an infectious disease, it is necessary to develop a stable, high-concentration protein formulation that provides dosing and administration advantages.

DETAILED DESCRIPTION OF INVENTION

Technical Problem

The present inventors developed a formulation with increased stability of a novel fusion protein dimer comprising, in one molecule, an IL-2 protein and a CD80 protein, thereby completing the present invention.

Solution to Problem

In order to achieve the above object, in an aspect of the present invention, there is provided a pharmaceutical formulation comprising a fusion protein dimer comprising an IL-2 protein and a CD80 protein.

Effects of Invention

A fusion protein dimer comprising an IL-2 protein and a CD80 protein can not only activate immune cells owing to IL-2, but also effectively regulate Treg cells owing to CD80. In order to use such a fusion protein dimer clinically, the stability of the protein preparation must be secured. When the pharmaceutical formulation according to the present invention is applied to a fusion protein dimer comprising an IL-2 protein and a CD80 protein, the stability of the fusion protein dimer is significantly increased, and it can be used as a liquid formulation. Accordingly, the commercial applicability of the fusion protein dimer can be increased.

BEST MODE FOR CARRYING OUT THE INVENTION

Figure 1:
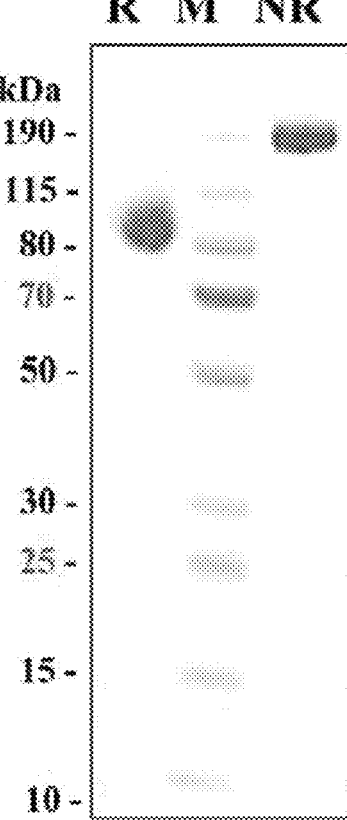
FIG. 1 illustrates a result detecting the obtained fusion protein (GI-101) with SDS-PAGE.

Pharmaceutical Formulation Comprising Fusion Protein Comprising IL-2 Protein and CD80 Protein In an aspect of the present invention, there is provided a pharmaceutical formulation comprising: (i) a fusion protein dimer comprising an IL-2 protein and a CD80 protein at a concentration of 3.0 mg/mL to 5.0 mg/mL; (ii) a buffer at a concentration of 10 mM to 30 mM; and (iii) a surfactant at a concentration of 0.155 w/w % to 0.185 w/w %; wherein the pH of the formulation is from 6.5 to 7.5.

Here, the pharmaceutical formulation may be a liquid formulation.

Fusion Protein Comprising IL-2 Protein and CD80 Protein

As used herein, the term "IL-2" or "interleukin-2", unless otherwise stated, refers to any wild-type IL-2 obtained from any vertebrate source, including mammals, for example, primates (such as humans) and rodents (such as mice and rats). IL-2 may be obtained from animal cells, and also includes one obtained from recombinant cells capable of producing IL-2. In addition, IL-2 may be wild-type IL-2 or a variant thereof.

In the present specification, IL-2 or a variant thereof may be collectively expressed by the term "IL-2 protein" or "IL-2 polypeptide." IL-2, an IL-2 protein, an IL-2 polypeptide, and an IL-2 variant specifically bind to, for example, an IL-2 receptor. This specific binding may be identified by methods known to those skilled in the art.

An embodiment of IL-2 may have the amino acid sequence of SEQ ID NO: 35 or SEQ ID NO: 36. Here, IL-2 may also be in a mature form. Specifically, the mature IL-2 may not contain a signal sequence, and may have the amino acid sequence of SEQ ID NO: 10. Here, IL-2 may be used under a concept encompassing a fragment of wild-type IL-2 in which a portion of N-terminus or C-terminus of the wild-type IL-2 is truncated.

In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 contiguous amino acids are truncated from N-terminus of a protein having the amino acid sequence of SEQ ID NO: 35 or SEQ ID NO: 36. In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 contiguous amino acids are truncated from C-terminus of a protein having the amino acid sequence of SEQ ID NO: 35 or SEQ ID NO: 36.

As used herein, the term "IL-2 variant" refers to a form in which a portion of amino acids in the full-length IL-2 or the above-described fragment of IL-2 is substituted. That is, an IL-2 variant may have an amino acid sequence different from wild-type IL-2 or a fragment thereof. However, an IL-2 variant may have activity equivalent or similar to the wild-type IL-2. Here, "IL-2 activity" may, for example, refer to specific binding to an IL-2 receptor, which specific binding can be measured by methods known to those skilled in the art.

Specifically, an IL-2 variant may be obtained by substitution of a portion of amino acids in the wild-type IL-2. An embodiment of the IL-2 variant obtained by amino acid substitution may be obtained by substitution of at least one of the $38^{th}$, $42^{nd}$, $45^{th}$, $61^{st}$, and $72^{nd}$ amino acids in the amino acid sequence of SEQ ID NO: 10.

Specifically, the IL-2 variant may be obtained by substitution of at least one of the $38^{th}$, $42^{nd}$, $45^{th}$, $61^{st}$, or $72^{nd}$ amino acid in the amino acid sequence of SEQ ID NO: 10 with another amino acid. In addition, when IL-2 is in a form in which a portion of N-terminus in the amino acid sequence of SEQ ID NO: 35 is truncated, the amino acid at a position complementarily corresponding to that in the amino acid sequence of SEQ ID NO: 10 may be substituted with another amino acid. For example, when IL-2 has the amino acid sequence of SEQ ID NO: 35, its IL-2 variant may be obtained by substitution of at least one of $58^{th}$, $62^{nd}$, $65^{th}$, $81^{st}$, or $92^{nd}$ amino acid in the amino acid sequence of SEQ ID NO: 35 with another amino acid. These amino acid residues correspond to the $38^{th}$, $42^{nd}$, $45^{th}$, $61^{st}$, and $72^{nd}$ amino acid residues in the amino acid sequence of SEQ ID NO: 10, respectively. According to an embodiment, one, two, three, four, five, six, seven, eight, nine, or ten amino acids may be substituted as long as such IL-2 variant maintains IL-2 activity. According to another embodiment, one to five amino acids may be substituted.

In an embodiment, an IL-2 variant may be in a form in which two amino acids are substituted. Specifically, the IL-2 variant may be obtained by substitution of the $38^{th}$ and $42^{nd}$ amino acids in the amino acid sequence of SEQ ID NO: 10. In addition, in an embodiment, the IL-2 variant may be obtained by substitution of the $38^{th}$ and $45^{th}$ amino acids in the amino acid sequence of SEQ ID NO: 10. In addition, in an embodiment, the IL-2 variant may be obtained by substitution of the $38^{th}$ and $61^{st}$ amino acids in the amino acid sequence of SEQ ID NO: 10. In addition, in an embodiment, the IL-2 variant may be obtained by substitution of the $38^{th}$ and $72^{nd}$ amino acids in the amino acid sequence of SEQ ID NO: 10. In addition, in an embodiment, the IL-2 variant may be obtained by substitution of the $42^{nd}$ and $45^{th}$ amino acids in the amino acid sequence of SEQ ID NO: 10. In addition, in an embodiment, the IL-2 variant may be obtained by substitution of the $42^{nd}$ and $61^{nd}$ amino acids in the amino acid sequence of SEQ ID NO: 10. In addition, in an embodiment, the IL-2 variant may be obtained by substitution of the $42^{nd}$ and $72^{nd}$ amino acids in the amino acid sequence of SEQ ID NO: 10. In addition, in an embodiment, the IL-2 variant may be obtained by substitution of the $45^{th}$ and $61^{nd}$ amino acids in the amino acid sequence of SEQ ID NO: 10. In addition, in an embodiment, the IL-2 variant may be obtained by substitution of the $45^{th}$ and $72^{nd}$ amino acids in the amino acid sequence of SEQ ID NO: 10. In addition, in an embodiment, the IL-2 variant may be obtained by substitution of the $61^{nd}$ and $72^{nd}$ amino acids in the amino acid sequence of SEQ ID NO: 10.

Furthermore, an IL-2 variant may be in a form in which three amino acids are substituted. Specifically, the IL-2 variant may be obtained by substitution of the $38^{th}$, $42^{nd}$ and $45^{th}$ amino acids in the amino acid sequence of SEQ ID NO: 10. In addition, in an embodiment, the IL-2 variant may be obtained by substitution of the $38^{th}$, $42^{nd}$, and $61^{nd}$ amino acids in the amino acid sequence of SEQ ID NO: 10. In addition, in an embodiment, the IL-2 variant may be obtained by substitution of the $38^{th}$, $42^{nd}$, and $72^{nd}$ amino acids in the amino acid sequence of SEQ ID NO: 10. In addition, in an embodiment, the IL-2 variant may be obtained by substitution of the $38^{th}$, $45^{th}$, and $61^{st}$ amino acids in the amino acid sequence of SEQ ID NO: 10. In addition, in an embodiment, the IL-2 variant may be obtained by substitution of the $38^{th}$, $45^{th}$, and $72^{nd}$ amino acids in the amino acid sequence of SEQ ID NO: 10. In addition, in an embodiment, the IL-2 variant may be obtained by substitution of the $38^{th}$, $61^{st}$, and $72^{nd}$ amino acids in the amino acid sequence of SEQ ID NO: 10. In addition, in an embodiment, the IL-2 variant may be obtained by substitution of the $42^{nd}$, $45^{th}$, and $61^{st}$ amino acids in the amino acid sequence of SEQ ID NO: 10. In addition, in an embodiment, the IL-2 variant may be obtained by substitution of the $42^{th}$, $45^{th}$, and $72^{nd}$ amino acids in the amino acid sequence of SEQ ID NO: 10. In addition, in an embodiment, the IL-2 variant may be obtained by substitution of the $45^{th}$, $61^{st}$, and $72^{nd}$ amino acids in the amino acid sequence of SEQ ID NO: 10.

In addition, an IL-2 variant may be in a form in which four amino acids are substituted. Specifically, the IL-2 variant may be obtained by substitution of the $38^{th}$, $42^{nd}$, $45^{th}$, and $61^{st}$ amino acids in the amino acid sequence of SEQ ID NO: 10. In addition, in an embodiment, the IL-2 variant may be obtained by substitution of the $38^{th}$, $42^{nd}$, $45^{th}$; and $72^{nd}$ amino acids in the amino acid sequence of SEQ ID NO: 10. In addition, in an embodiment, the IL-2 variant may be obtained by substitution of the $38^{th}$, $45^{th}$, $61^{st}$, and $72^{nd}$ amino acids in the amino acid sequence of SEQ ID NO: 10. In addition, in an embodiment, the IL-2 variant may be obtained by substitution of the $38^{th}$, $42^{nd}$, $61^{st}$, and $72^{nd}$ amino acids in the amino acid sequence of SEQ ID NO: 10. In addition, in an embodiment, the IL-2 variant may be obtained by substitution of $42^{nd}$, $45^{th}$, $61^{st}$, and $72^{nd}$ amino acids in the amino acid sequence of SEQ ID NO: 10.

Furthermore, an IL-2 variant may be in a form in which five amino acids are substituted. Specifically, the IL-2 variant may be obtained by substitution of each of the $38^{th}$, $42^{nd}$, $45^{th}$, $61^{st}$, and $72^{nd}$ amino acids in the amino acid sequence of SEQ ID NO: 10 with another amino acid.

Here, the "another amino acid" introduced by the substitution may be any one selected from the group consisting of alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine. However, regarding amino acid substitution for the IL-2 variant, in the amino acid sequence of SEQ ID NO: 10, the $38^{th}$ amino acid cannot be substituted with arginine, the $42^{nd}$ amino acid cannot be substituted with phenylalanine, the $45^{th}$ amino acid cannot be substituted with tyrosine, the $61^{st}$ amino acid cannot be substituted with glutamic acid, and the $72^{nd}$ amino acid cannot be substituted with leucine.

Regarding amino acid substitution for an IL-2 variant, in the amino acid sequence of SEQ ID NO: 10, the $38^{th}$ amino acid, arginine, may be substituted with an amino acid other than arginine. Preferably, regarding amino acid substitution for an IL-2 variant, in the amino acid sequence of SEQ ID NO: 10, the $38^{th}$ amino acid, arginine, may be substituted with alanine (R38A).

Regarding amino acid substitution for an IL-2 variant, in the amino acid sequence of SEQ ID NO: 10, the $42^{nd}$ amino acid, phenylalanine, may be substituted with an amino acid other than phenylalanine. Preferably, regarding amino acid substitution for an IL-2 variant, in the amino acid sequence of SEQ ID NO: 10, the $42^{nd}$ amino acid, phenylalanine, may be substituted with alanine (F42A).

Regarding amino acid substitution for an IL-2 variant, in the amino acid sequence of SEQ ID NO: 10, the $45^{th}$ amino acid, tyrosine, may be substituted with an amino acid other than tyrosine. Preferably, regarding amino acid substitution for an IL-2 variant, in the amino acid sequence of SEQ ID NO: 10, the $45^{th}$ amino acid, tyrosine, may be substituted with alanine (Y45A).

Regarding amino acid substitution for an IL-2 variant, in the amino acid sequence of SEQ ID NO: 10, the $61^{nd}$ amino acid, glutamic acid, may be substituted with an amino acid other than glutamic acid. Preferably, regarding amino acid substitution for an IL-2 variant, in the amino acid sequence of SEQ ID NO: 10, the $61^{st}$ amino acid, glutamic acid, may be substituted with arginine (E61R).

Regarding amino acid substitution for an IL-2 variant, in the amino acid sequence of SEQ ID NO: 10, the $72^{nd}$ amino acid, leucine, may be substituted with an amino acid other than leucine. Preferably, regarding amino acid substitution for an IL-2 variant, in the amino acid sequence of SEQ ID NO: 10, the $72^{nd}$ amino acid, leucine, may be substituted with glycine (L72G).

Specifically, an IL-2 variant may be obtained by at least one substitution selected from the group consisting of R38A, F42A, Y45A, E61R, and L72G, in the amino acid sequence of SEQ ID NO: 10.

Specifically, an IL-2 variant may be obtained by amino acid substitutions at two, three, four, or five positions among the positions selected from the group consisting of R38A, F42A, Y45A, E61R, and L72G.

In addition, an IL-2 variant may be in a form in which two amino acids are substituted. Specifically, an IL-2 variant may be obtained by the substitutions, R38A and F42A. In addition, in an embodiment, an IL-2 variant may be obtained by the substitutions, R38A and Y45A. In addition, in an embodiment, an IL-2 variant may be obtained by the substitutions, R38A and E61R. In addition, in an embodiment, an IL-2 variant may be obtained by the substitutions, R38A and L72G. In addition, in an embodiment, an IL-2 variant may be obtained by the substitutions, F42A and Y45A. In addition, in an embodiment, an IL-2 variant may be obtained by the substitutions, F42A and E61R. In addition, in an embodiment, an IL-2 variant may be obtained by the substitutions, F42A and L72G. In addition, in an embodiment, an IL-2 variant may be obtained by the substitutions, E61R and L72G.

Furthermore, an IL-2 variant may be in a form in which three amino acids are substituted. Specifically, an IL-2 variant may be obtained by the substitutions, R38A, F42A, and Y45A. In addition, in an embodiment, an IL-2 variant may be obtained by the substitutions, R38A, F42A, and E61R. In addition, in an embodiment, an IL-2 variant may be obtained by the substitutions, R38A, F42A, and L72G. In addition, in an embodiment, an IL-2 variant may be obtained by the substitutions, R38A, Y45A, and E61R. In addition, in an embodiment, an IL-2 variant may be obtained by the substitutions, R38A, Y45A, and L72G. In addition, in an embodiment, an IL-2 variant may be obtained by the substitutions, F42A, Y45A, and E61R. In addition, in an embodiment, an IL-2 variant may be obtained by the substitutions, F42A, Y45A, and L72G. In addition, in an embodiment, an IL-2 variant may be obtained by the substitutions, F42A, E61R, and L72G. In addition, in an embodiment, an IL-2 variant may be obtained by the substitutions, Y45A, E61R, and L72G.

In addition, an IL-2 variant may be in a form in which four amino acids are substituted. Specifically, an IL-2 variant may be obtained by the substitutions, R38A, F42A, Y45A, and E61R. In addition, in an embodiment, an IL-2 variant may be obtained by the substitutions, R38A, F42A, Y45A, and L72G. In addition, in an embodiment, an IL-2 variant may be obtained by the substitutions, R38A, F42A, E61R, and L72G. In addition, in an embodiment, an IL-2 variant may be obtained by the substitutions, R38A, Y45A, E61R, and L72G. In addition, in an embodiment, an IL-2 variant may be obtained by the substitutions, F42A, Y45A, E61R, and L72G.

Furthermore, an IL-2 variant may be obtained by the substitutions, R38A, F42A, Y45A, E61R, and L72G.

Preferably, an embodiment of the IL-2 variant may contain which are any one selected from the following substitution combinations (a) to (d) in the amino acid sequence of SEQ ID NO: 10:
(a) R38A/F42A
(b) R38A/F42A/Y45A
(c) R38A/F42A/E61R
(d) R38A/F42A/L72G Here, when IL-2 has the amino acid sequence of SEQ ID NO: 35, an amino acid substitution may be present at a position complementarily corresponding to that in the amino acid sequence of SEQ ID NO: 10. In addition, even when IL-2 is a fragment of the amino acid sequence of SEQ ID NO: 35, an amino acid substitution may be present at a position complementarily corresponding to that in the amino acid sequence of SEQ ID NO: 10.

Specifically, an IL-2 variant may have the amino acid sequence of SEQ ID NO: 6, 22, 23, or 24.

In addition, an IL-2 variant may be characterized by having low in vivo toxicity. Here, the low in vivo toxicity may be a side effect caused by binding of IL-2 to the IL-2 receptor alpha chain (IL-2Ra). Various IL-2 variants have been developed to ameliorate the side effect caused by binding of IL-2 to IL-2Rα, and such IL-2 variants may be those disclosed in U.S. Pat. No. 5,229,109 and Korean Patent No. 1667096. In particular, IL-2 variants described in the present application have low binding ability for the IL-2 receptor alpha chain (IL-2Rα) and thus have lower in vivo toxicity than the wild-type IL-2.

As used herein, the term "CD80", also called "B7-1", is a membrane protein present in dendritic cells, activated B cells, and monocytes. CD80 provides co-stimulatory signals essential for activation and survival of T cells. CD80 is known as a ligand for the two different proteins, CD28 and CTLA-4, present on the surface of T cells. CD80 is composed of 288 amino acids, and may specifically have the amino acid sequence of SEQ ID NO: 11. In addition, as used herein, the term "CD80 protein" refers to the full-length CD80 or a CD80 fragment.

As used herein, the term "CD80 fragment" refers to a cleaved form of CD80. In addition, the CD80 fragment may be an extracellular domain of CD80. An embodiment of the CD80 fragment may be obtained by elimination of the $1^{st}$ to $34^{th}$ amino acids from N-terminus which are a signal sequence of CD80. Specifically, an embodiment of the CD80 fragment may be a protein composed of the $35^{th}$ to $288^{th}$ amino acids in SEQ ID NO: 11.

In addition, an embodiment of the CD80 fragment may be a protein composed of the $35^{th}$ to $242^{nd}$ amino acids in SEQ ID NO: 11. In addition, an embodiment of the CD80 fragment may be a protein composed of the $35^{th}$ to $232^{nd}$ amino acids in SEQ ID NO: 11. In addition, an embodiment of the CD80 fragment may be a protein composed of the $35^{th}$ to $139^{th}$ amino acids in SEQ ID NO: 11. In addition, an embodiment of the CD80 fragment may be a protein composed of the $142^{nd}$ to $242^{nd}$ amino acids in SEQ ID NO: 11. In an embodiment, a CD80 fragment may have the amino acid sequence of SEQ ID NO: 2.

In addition, the IL-2 protein and the CD80 protein may be attached to each other via a linker or a carrier. Specifically, the IL-2 or a variant thereof and the CD80 (B7-1) or a fragment thereof may be attached to each other via a linker or a carrier. In the present description, the linker and the carrier may be used interchangeably.

The linker links two proteins. An embodiment of the linker may include 1 to 50 amino acids, albumin or a fragment thereof, an Fc domain of an immunoglobulin, or the like. Here, the Fc domain of immunoglobulin refers to a protein that contains heavy chain constant region 2 (CH2) and heavy chain constant region 3 (CH3) of an immunoglobulin, and does not contain heavy and light chain variable regions and light chain constant region 1 (CH1) of an immunoglobulin. The immunoglobulin may be IgG, IgA, IgE, IgD, or IgM, and may preferably be IgG4. Here, Fc domain of wild-type immunoglobulin G4 may have the amino acid sequence of SEQ ID NO: 4.

In addition, the Fc domain of an immunoglobulin may be an Fc domain variant as well as wild-type Fc domain. In addition, as used herein, the term "Fc domain variant" may refer to a form which is different from the wild-type Fc domain in terms of glycosylation pattern, has a high glycosylation as compared with the wild-type Fc domain, or has a low glycosylation as compared with the wild-type Fc domain, or a deglycosylated form. In addition, an aglycosylated Fc domain is included therein. The Fc domain or a variant thereof may be adapted to have an adjusted number of sialic acids, fucosylations, or glycosylations, through culture conditions or genetic manipulation of a host. In addition, glycosylation of the Fc domain of an immunoglobulin may be modified by conventional methods such as chemical methods, enzymatic methods, and genetic engineering methods using microorganisms. In addition, the Fc domain variant may be in a mixed form of respective Fc regions of immunoglobulins, IgG, IgA, IgE, IgD, and IgM. In addition, the Fc domain variant may be in a form in which some amino acids of the Fc domain are substituted with other amino acids. An embodiment of the Fc domain variant may have the amino acid sequence of SEQ ID NO: 12.

The fusion protein may have a structure in which, using an Fc domain as a linker (or carrier), a CD80 protein and an IL-2 protein, or an IL-2 protein and a CD80 protein are linked to N-terminus and C-terminus of the linker or carrier, respectively. Linkage between N-terminus or C-terminus of the Fc domain and CD-80 or IL-2 may optionally be achieved by a linker peptide.

Specifically, a fusion protein may consist of the following structural formula (I) or (II):

$$N'\text{-}X\text{-}[linker(1)]_n\text{-}Fc\ domain\text{-}[linker(2)]_m\text{-}Y\text{-}C' \qquad (I)$$

$$N'\text{-}Y\text{-}[linker(1)]_n\text{-}Fc\ domain\text{-}[linker(2)]_m\text{-}X\text{-}C' \qquad (II)$$

Here, in the structural formulas (I) and (II),
N' is the N-terminus of the fusion protein,
C' is the C-terminus of the fusion protein,
X is a CD80 protein,
Y is an IL-2 protein,
the linkers (1) and (2) are peptide linkers, and
n and m are each independently 0 or 1.

Preferably, the fusion protein may consist of the structural formula (I). The IL-2 protein is as described above. In addition, the CD80 protein is as described above. According to an embodiment, the IL-2 protein may be an IL-2 variant with one to five amino acid substitutions as compared with the wild-type IL-2. The CD80 protein may be a fragment obtained by truncation of up to about 34 contiguous amino acid residues from the N-terminus or C-terminus of the wild-type CD80. Alternatively, the CD protein may be an extracellular immunoglobulin-like domain having the activity of binding to the T cell surface receptors CTLA-4 and CD28.

Specifically, the fusion protein may have the amino acid sequence of SEQ ID NO: 9, 26, 28, or 30. According to another embodiment, the fusion protein includes a polypeptide having a sequence identity of 85%, 86%, 87%, 88%, 89%, 90%, 91%, 92%, 93%, 94%, 95%, 96%, 97%, 98%, 99%, or 100% to the amino acid sequence of SEQ ID NO: 9, 26, 28, or 30. Here, the identity is, for example, percent homology, and may be determined through homology comparison software such as BlastN software of the National Center of Biotechnology Information (NCBI).

The peptide linker (1) may be included between the CD80 protein and the Fc domain. The peptide linker (1) may consist of 5 to 80 contiguous amino acids, 20 to 60 contiguous amino acids, 25 to 50 contiguous amino acids, or 30 to 40 contiguous amino acids. In an embodiment, the peptide linker (1) may consist of 30 amino acids. In addition, the peptide linker (1) may contain at least one cysteine. Specifically, the peptide linker (1) may contain one, two, or three cysteines. In addition, the peptide linker (1) may be derived from the hinge of an immunoglobulin. In an embodiment, the peptide linker (1) may be a peptide linker consisting of the amino acid sequence of SEQ ID NO: 3.

The peptide linker (2) may consist of 1 to 50 contiguous amino acids, 3 to 30 contiguous amino acids, or 5 to 15 contiguous amino acids. In an embodiment, the peptide linker (2) may be $(G4S)_n$ (where n is an integer of 1 to 10). Here, in $(G4S)_n$, n may be 1, 2, 3, 4, 5, 6, 7, 8, 9, or 10. In an embodiment, the peptide linker (2) may be a peptide linker consisting of the amino acid sequence of SEQ ID NO: 5.

In another aspect of the present invention, there is provided a dimer obtained by binding of two fusion proteins, each of which comprises an IL-2 protein and a CD80 protein. The fusion protein comprising IL-2 or a variant thereof and CD80 or a fragment thereof is as described above.

Here, the binding between the fusion proteins constituting the dimer may be achieved by, but is not limited to, a disulfide bond formed by cysteines present in the linker. The fusion proteins constituting the dimer may be the same or different fusion proteins from each other. Preferably, the dimer may be a homodimer. An embodiment of the fusion protein constituting the dimer may be a protein having the amino acid sequence of SEQ ID NO: 9.

Pharmaceutical Formulation

In an aspect of the present invention, there is provided a pharmaceutical formulation comprising the fusion protein dimer comprising an IL-2 protein and a CD80 protein.

As used herein, the term "pharmaceutical formulation" refers to a preparation that exists in a form that allows the biological activity of an active ingredient to be clearly effective, and does not contain an ingredient that causes side effects in a subject to which the formulation is administered.

The term "subject" may be a mammal such as human, dog, cow, horse, pig, sheep, goat, cat, mouse, rabbit, and rat, and may be preferably human, dog, or cat.

As used herein, the term "pharmaceutical formulation" refers to a pharmaceutical formulation that uses a suitable aqueous solvent, such as water or an aqueous/oily mixture (for example, a water alcohol mixture). The formulation may maintain stability, such as chemical or physical stability, biological activity.

The term "stability" refers to a property that maintains a constant state, and is generally related to minimize degradation, denaturation, aggregation, or unfolding of a biologically active substance, such as a protein, a peptide or a biologically active macromolecule.

Meanwhile, the formulation may be a liquid formulation. The liquid formulation is a aqueous solution or suspension, and may be stably maintained at room temperature, refrigerated (for example, 2° C. to 8° C.) or frozen (for example, −20° C. or −70° C.) during storage.

The pharmaceutical formulation of the present invention may be administered parenterally. Here, parenteral administration may be performed by a method such as subcutaneous administration, intravenous administration, mucosal administration, and intramuscular administration. In an embodiment of the present invention, the formulation may be preferably administered by intravenous injection.

The fusion protein dimer in the pharmaceutical formulation may be at a concentration of 3.0 mg/mL to 5.0 mg/mL. In addition, the fusion protein dimer may be at a concentration of 3.0 mg/mL to 4.8 mg/mL, at a concentration of 3.0 mg/mL to 4.6 mg/mL, at a concentration of 3.0 mg/mL to 4.4 mg/mL, at a concentration of 3.0 mg/mL to 4.2 mg/mL, at a concentration of 3.2 mg/mL to 4.8 mg/mL, at a concentration of 3.2 mg/mL to 4.6 mg/mL, at a concentration of 3.2 mg/mL to 4.4 mg/mL, at a concentration of 3.2 mg/mL to 4.2 mg/mL, at a concentration of 3.4 mg/mL to 4.8 mg/mL, at a concentration of 3.4 mg/mL to 4.6 mg/mL, at a concentration of 3.4 mg/mL to 4.4 mg/mL, at a concentration of 3.4 mg/mL to 4.2 mg/mL, at a concentration of 3.6 mg/mL to 4.8 mg/mL, at a concentration of 3.6 mg/mL to 4.6 mg/mL, at a concentration of 3.6 mg/mL to 4.4 mg/mL, at a concentration of 3.6 mg/mL to 4.2 mg/mL, at a concentration of 3.8 mg/mL to 4.8 mg/mL, at a concentration of 3.8 mg/mL to 4.6 mg/mL, at a concentration of 3.8 mg/mL to 4.4 mg/mL, at a concentration of 3.8 mg/mL to 4.2 mg/mL, or at a concentration of 3.9 mg/mL to 4.1 mg/mL. Specifically, the fusion protein dimer may be at a concentration of 4.0 mg/mL.

In addition, the buffer may be a histidine buffer. Here, the histidine may be at a concentration of 10 mM to 30 mM. In addition, the histidine may be at a concentration of 10 mM to 28 mM, at a concentration of 10 mM to 26 mM, at a concentration of 10 mM to 24 mM, at a concentration of 10 mM to 22 mM, at a concentration of 10 mM to 21 mM, at a concentration of 12 mM to 28 mM, at a concentration of 12 mM to 26 mM, at a concentration of 12 mM to 24 mM, at a concentration of 12 mM to 22 mM, at a concentration of 12 mM to 21 mM, at a concentration of 14 mM to 28 mM, at a concentration of 14 mM to 26 mM, at a concentration of 14 mM to 24 mM, at a concentration of 14 mM to 22 mM, at a concentration of 14 mM to 21 mM, at a concentration of 16 mM to 28 mM, at a concentration of 16 mM to 26 mM, at a concentration of 16 mM to 24 mM, at a concentration of 16 mM to 22 mM, at a concentration of 16 mM to 21 mM, at a concentration of 18 mM to 28 mM, at a concentration of 18 mM to 26 mM, at a concentration of 18 mM to 24 mM, at a concentration of 18 mM to 22 mM, at a concentration of 18 mM to 21 mM, at a concentration of 19 mM to 28 mM, at a concentration of 19 mM to 26 mM, at a concentration of 19 mM to 24 mM, at a concentration of 19 mM to 22 mM, or at a concentration of 19 mM to 21 mM. Specifically, the histidine may be at a concentration of 20 mM.

In addition, the pH of the pharmaceutical formulation may be from 6.5 to 7.5. In addition, the pH of the pharmaceutical formulation may be from 6.5 to 7.3, from 6.5 to 7.2, from 6.5 to 7.1, from 6.7 to 7.3, from 6.7 to 7.2, from 6.7 to 7.1, from 6.8 to 7.3, from 6.8 to 7.2, from 6.8 to 7.1, from 6.9 to 7.3, from 6.9 to 7.2, or from 6.9 to 7.1. Preferably, the pH of the pharmaceutical formulation may be 7.0.

In addition, the surfactant of the pharmaceutical formulation may include any one selected from the group consisting of polysorbate (e.g.: polysorbate 20, polysorbate 28, polysorbate 40, polysorbate 60, polysorbate 65, polysorbate 80, polysorbate 81, and polysorbate 85); poloxamer (e.g.: poloxamer 181, poloxamer 188, and poloxamer 407); polyethylene glycol (PEG); and a combination thereof. Preferably, the pharmaceutical formulation may include two of the surfactants.

In addition, the surfactant may be included at a concentration of 0.065 w/w % to 0.2 w/w % in the formulation. In addition, the surfactant may be included at a concentration of 0.155 w/w % to 0.185 w/w % in the formulation. In an embodiment, the surfactant may be poloxamer 188. Here, the surfactant may be included at a concentration of 0.065 w/w % to 0.075 w/w % in the formulation. In addition, in an embodiment, the surfactant may be polysorbate 80. Here, the surfactant may be included at a concentration of about 0.09 w/w % to about 0.11 w/w % in the formulation. Preferably, poloxamer 188 and polysorbate 80 may be included in the formulation, and they may be included at a concentration of 0.065 w/w % to 0.075 w/w % and at a concentration of 0.09 w/w % to about 0.11 w/w %, respectively. Specifically, poloxamer 188 and polysorbate 80 may be included at a concentration of 0.07 w/w % and 0.1 w/w % in the formulation, respectively.

In addition, the pharmaceutical formulation may further comprise an amino acid. The amino acid may be any one selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan.

Here, the amino acid may be at a concentration of 10 mg/mL to 30 mg/mL. In addition, the amino acid may be at a concentration of 10 mg/mL to 25 mg/mL, at a concentration of 10 mg/mL to 20 mg/mL, at a concentration of 10 mg/mL to 18 mg/mL, at a concentration of 10 mg/mL to 16 mg/mL, at a concentration of 12 mg/mL to 25 mg/mL, at a concentration of 12 mg/mL to 20 mg/mL, at a concentration of 12 mg/mL to 18 mg/mL, at a concentration of 12 mg/mL to 16 mg/mL, at a concentration of 14 mg/mL to 25 mg/mL, at a concentration of 14 mg/mL to 20 mg/mL, at a concentration of 14 mg/mL to 18 mg/mL, or at a concentration of 14 mg/mL to 16 mg/mL. Specifically, the amino acid may be at a concentration of 15 mg/mL.

In an embodiment, the amino acid may be arginine, and may be preferably arginine-HCl. Here, the arginine may be included at a concentration of 14 mg/mL to 16 mg/mL, and may be preferably included at a concentration of 15 mg/mL.

In addition, the pharmaceutical formulation may further comprise a sugar. The sugar may be any one selected from the group consisting of sucrose, sorbitol, glycerol, trehalose, and mannitol. Here, the sugar may be included at a concentration of 120 mg/mL to 180 mg/mL. In addition, the sugar may be at a concentration of 120 mg/mL to 170 mg/mL, at a concentration of 120 mg/mL to 160 mg/mL, at a concentration of 120 mg/mL to 155 mg/mL, at a concentration of 130 mg/mL to 170 mg/mL, at a concentration of 130 mg/mL to 160 mg/mL, at a concentration of 130 mg/mL to 155 mg/mL, at a concentration of 135 mg/mL to 170 mg/mL, at a concentration of 135 mg/mL to 160 mg/mL, at a concentration of 135 mg/mL to 155 mg/mL, at a concentration of 140 mg/mL to 170 mg/mL, at a concentration of 140 mg/mL to 160 mg/mL, at a concentration of 140 mg/mL to 155 mg/mL, at a concentration of 145 mg/mL to 170 mg/mL, at a concentration of 145 mg/mL to 160 mg/mL, or at a concentration of 145 mg/mL to 155 mg/mL.

In an embodiment, the sugar may be sucrose, and the sucrose may be at a concentration of 150 mg/mL.

In an embodiment of the present invention, the pharmaceutical formulation may comprise (i) a fusion protein dimer comprising an IL-2 protein and a CD80 protein at a concentration of 3.0 mg/mL to 5.0 mg/mL; (ii) histidine at a concentration of 10 mM to 30 mM; (iii) poloxamer 188 at a concentration of 0.065 w/w % to 0.075 w/w %; (iv) polysorbate 80 at a concentration of 0.09 w/w % to 0.11 w/w %; (v) arginine at a concentration of 10 mg/mL to 30 mg/mL; and (vi) sucrose at a concentration of 120 mg/mL to 180 mg/mL, wherein the pH of the pharmaceutical formulation may be from 6.5 to 7.5.

The pharmaceutical formulation may be stored in a container selected from the group consisting of a vial, a cartridge, a syringe, and an autoinjector.

In addition, the container in which the formulation is stored may be stored at room temperature, at 2° C. to 8° C., or at 25° C. to 40° C. until administered to a subject in need of treatment.

The subject may be a mammal such as human, dog, cow, horse, pig, sheep, goat, cat, mouse, rabbit, and rat, and may be preferably human.

The formulation may be administered by parenteral administration such as subcutaneous administration, intravenous administration, mucosal administration, intramuscular administration, or intraperitoneal administration, but not limited thereto. Preferably, it may be intravenously administered.

MODE FOR CARRYING OUT THE INVENTION

Hereinafter, the present invention will be described in more detail by way of the following examples. However, the following examples are only for illustrating the present invention, and the scope of the present invention is not limited thereto.

Preparation Example 1. Preparation of hCD80-Fc-IL-2 Variant (2M): GI-101

In order to produce a fusion protein dimer comprising a human CD80 fragment, an Fc domain, and an IL-2 variant, a polynucleotide was synthesized through the Invitrogen GeneArt Gene Synthesis service of ThermoFisher Scientific. Specifically, the polynucleotide contains a nucleotide sequence (SEQ ID NO: 8) which encodes a fusion protein that contains a signal peptide (SEQ ID NO: 1), a CD80 fragment (SEQ ID NO: 2), an Ig hinge (SEQ ID NO: 3) to which a linker is bound, an Fc domain (SEQ ID NO: 4), a linker (SEQ ID NO: 5), and an IL-2 variant (2M) (R38A, F42A) (SEQ ID NO: 6) having two amino acid substitutions, in this order, from the N-terminus. The polynucleotide was inserted into pcDNA3_4 vector. In addition, the vector was introduced into CHO cells (Expi-CHO™) to express the fusion protein of SEQ ID NO: 9. After the vector was introduced, culture was performed for 7 days under the condition of 37° C., 125 RPM, and 8% $CO_2$. Then, the culture was collected and the fusion protein was purified therefrom. The purified fusion protein was designated "GI-101".

Purification was carried out using chromatography containing MabSelect SuRe protein A resin. The fusion protein was bound thereto under a condition of 25 mM Tris, and 25 mM NaCl, and pH 7.4. Then, elution was performed with 100 mM NaCl and 100 mM acetic acid (pH 3). 20% 1 M Tris-HCl at pH 9 was placed in a collection tube, and then the fusion protein dimer was collected. For the collected fusion protein dimer, the buffer was exchanged through dialysis with PBS buffer for 16 hours.

Figure 2:
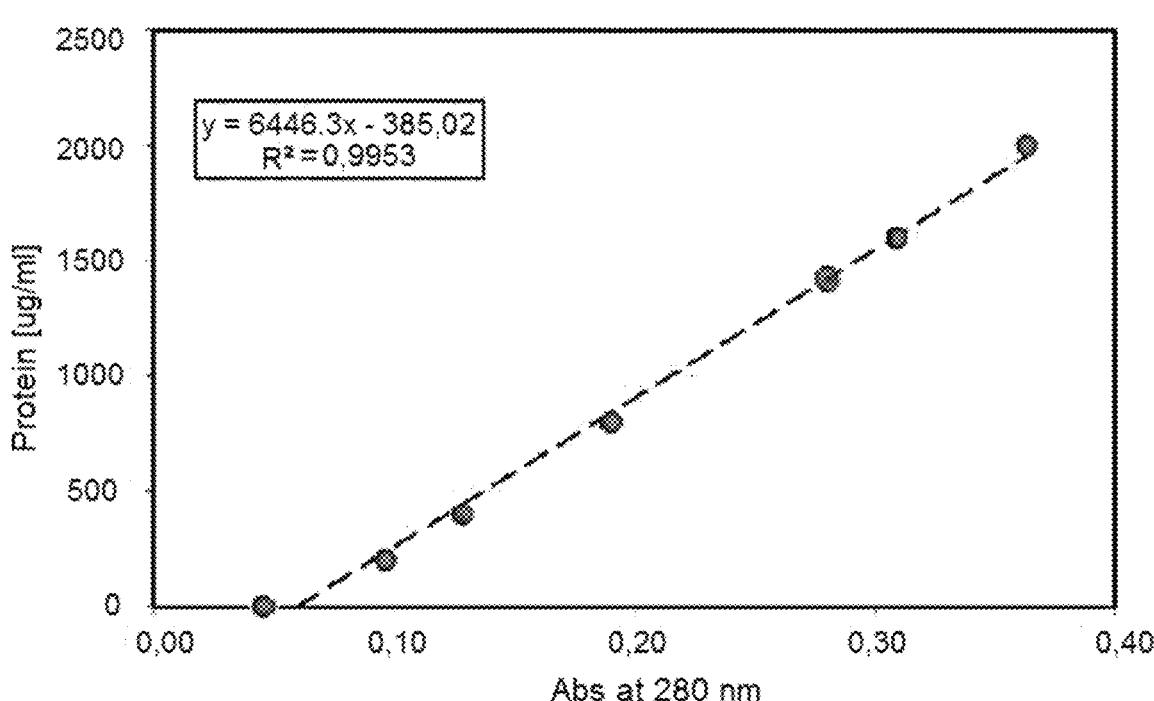
FIG. 2 illustrates amounts of the fusion protein (GI-101) depending on absorbance.
Figure 3:
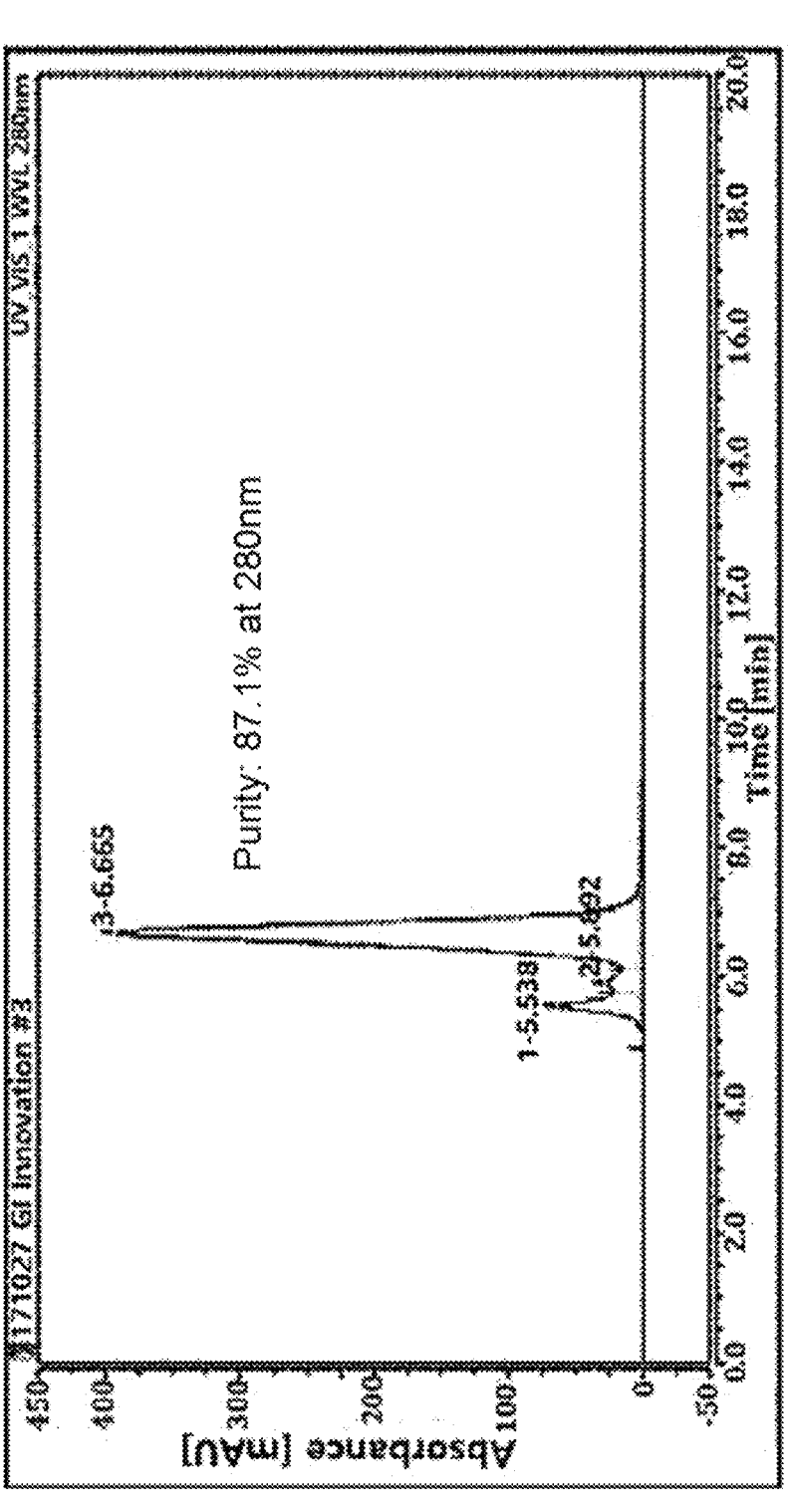
FIG. 3 illustrates a result analyzing the obtained fusion protein (GI-101) by size exclusion chromatography (SEC).

Thereafter, absorbance at 280 nm wavelength was measured, over time, with size exclusion chromatography using a TSKgel G3000SWXL column (TOSOH Bioscience), to obtain a highly concentrated fusion protein dimer. Here, the isolated and purified fusion protein dimer was subjected to SDS-PAGE under reduced (R) or non-reduced (NR) condition, and stained with Coomassie Blue to check its purity (FIG. 1). It was identified that the fusion protein dimer was contained at a concentration of 2.78 mg/ml when detected with NanoDrop (FIG. 2). In addition, the results obtained by analysis using size exclusion chromatography are provided in FIG. 3.

Example 1. Evaluation of Optimal Buffer/pH Condition

In order to determine the optimal buffer/pH for the liquid formulation containing the fusion protein dimer (GI-101) of a CD80 protein and an IL-2 protein, a total of eight buffer/pH were screened. A stability test (40° C., 2 weeks) was performed to select the optimal buffer/pH.

The buffer/pH screening samples were stored at 40° C. for 2 weeks, and then the samples were analyzed using size exclusion chromatography (SEC). In order to identify the size exclusion profile of the GI-101 protein, SEC was performed using HPLC (Waters, e2695 and Thermo scientific, Ultimate 3000). The % area of the monomer was calculated using a chromatogram at 214 nm.

During formulation development, the SEC profile was used to aim at maximizing the % monomer. The stability test results for buffer/pH screening are summarized in Table 1. Sample #6 containing histidine buffer, pH 7.0 exhibited less change than the other samples.

TABLE 1

| No. | Buffer | SEC (% monomer) | Rate of change (%)* |
|---|---|---|---|
| 1 | citrate buffer, pH 4.5 | 0.00 | −100 |
| 2 | citrate buffer, pH 5.0 | 0.00 | −100 |
| 3 | histidine buffer, pH 5.5 | 0.00 | −100 |
| 4 | histidine buffer, pH 6.0 | 10.60 | −88.52 |
| 5 | histidine buffer, pH 6.5 | 6.48 | −92.95 |
| 6 | histidine buffer, pH 7.0 | 36.91 | −60.15 |
| 7 | phosphate buffer, pH 7.0 | 8.46 | −90.76 |
| 8 | phosphate buffer, pH 7.5 | 0.00 | −100 |

*Rate of change = (data after storage at 40° C. for 2 weeks − initial data)/initial data × 100

Based on the stability test data, a histidine buffer at pH 7.0 was determined as a buffer for GI-101.

TABLE 2

| Composition | Concentration |
|---|---|
| histidine buffer, pH 7.0 | 20 mM |

Example 2. Excipient Screening Test

Example 2.1. Excipient Screening

In order to determine the excipient for the liquid formulation containing GI-101, an excipient screening test was performed under the buffer/pH (histidine buffer, pH 7.0) condition selected in Example 1.

For 8 different excipients [Polysorbate 80, Poloxamer 188, arginine-HCl (L-Arginine Monohydrochloride), L-Methionine, D-Mannitol, Sorbitol, Sucrose, and D-(+)-Trehalose Dihydrate], the results of Tm & Tagg, SEC and visual particle test obtained by performing under 5 different test conditions were statistically analyzed to select poloxamer 188, arginine-HCl, and sucrose as excipients.

TABLE 3

| Type of excipient | Surfactant | Amino acid | Sugar |
|---|---|---|---|
| Selected | poloxamer 188 | arginine-HCl | sucrose |

Example 2.2. Screening for Optimal Excipient Concentration

According to Example 2.1., poloxamer 188, arginine-HCl, and sucrose were selected as excipients for the liquid formulation containing GI-101.

Screening tests were performed under 16 conditions by varying the concentration of each excipient in order to find the optimal concentration for the combination of the three excipients.

Example 2.2.1. Thermal Stability Test (40° C., 2 Weeks)

Sixteen excipient screening test samples were stored at 40° C. for 2 weeks, and then the samples were analyzed through the protein concentration (A280) and SEC tests. The results are shown in Table 4.

TABLE 4

| | A280 | | SEC | |
| No. | Protein concentration (mg/mL) | Rate of change (%) | Monomer (%) | Rate of change (%) |
|---|---|---|---|---|
| 1 | 8.38 | 1.3% | 42.86 | −54.4% |
| 2 | 8.45 | −0.2% | 67.26 | −28.3% |
| 3 | 8.69 | 4.8% | 14.42 | −84.6% |
| 4 | 8.37 | 0.2% | 63.08 | −32.6% |
| 5 | 8.33 | −1.9% | 63.37 | −32.5% |
| 6 | 8.45 | 1.7% | 42.86 | −53.9% |
| 7 | 8.74 | 4.8% | 14.97 | −84.1% |
| 8 | 8.46 | 1.2% | 38.19 | −59.2% |
| 9 | 8.46 | 1.3% | 64.98 | −30.6% |
| 10 | 8.35 | −1.1% | 81.92 | −12.5% |
| 11 | 8.44 | 0.2% | 81.28 | −12.8% |
| 12 | 8.45 | 0.5% | 61.95 | −33.6% |
| 13 | 8.49 | 0.1% | 65.6 | −30.0% |
| 14 | 8.43 | 0.8% | 65.26 | −30.3% |
| 15 | 8.45 | 1.4% | 39.29 | −58.1% |
| 16 | 8.41 | 0.5% | 80.12 | −14.4% |

Example 2.2.2. RSM and Simulation Results

RSM (Response surface model) was used to determine the optimal concentration of each excipient. The optimal reaction could be found by adjusting the concentration of each excipient in the prediction profiler. In the results predicted by the prediction profiler, the concentration of sucrose was set to be the optimal value of 150 mg/mL, which is the maximum value of the experiment. Therefore, only arginine-HCl and poloxamer 188 concentrations were set by simulation. The predicted optimal concentration range of each excipient is shown in Table 5.

TABLE 5

| Excipient | Range |
|---|---|
| poloxamer 188 | 0.05 to 0.075 w/w % |
| arginine-HCl | 10 to 20 mg/mL |
| sucrose | 150 mg/mL |

Example 2.3. Final Stability Test (4 Weeks)

Based on the optimal concentration range for each excipient in Table 5, the final formulation candidates in Table 6 were derived. The final 4 weeks stability test was performed on the formulation candidates in Table 6.

TABLE 6

| Excipient | Poloxamer 188 | Arginine-HCl | Sucrose |
|---|---|---|---|
| Optimal condition | 0.07 w/w % | 15 mg/mL | 150 mg/mL |
| Target range | 0.065 to 0.075 w/w % | 14 to 16 mg/mL | 140 to 160 mg/mL |

The stability of the formulation candidates was tested under a total of five different conditions. Immediately after preparing samples, the release test (t=0) was performed, and candidate samples were stored for 4 weeks at 5° C. (long-term condition), −70° C. (long-term second condition), 25° C. (accelerated condition), and 40° C. (severe condition), respectively. In particular, in the case of the 40° C. stability test (severe condition), an additional sample was taken at 2-week time point in order to identify the change trend. After storing for 4 weeks under each condition, the samples were analyzed through SEC, protein concentration (A280) and pH tests. The final stability test results for the GI-101 formulation candidate are shown in Table 7.

TABLE 7

| Test condition | Protein concentration (mg/mL) | pH | SEC (% monomer) |
|---|---|---|---|
| Long-term condition (5° C., 4 weeks) | 8.01 | 7.11 | 94.50 |
| Long-term second condition (−70° C., 4 weeks) | 8.01 | 7.08 | 94.30 |
| Accelerated condition (25° C., 4 weeks) | 8.05 | 7.11 | 94.90 |

TABLE 7-continued

| Test condition | Protein concentration (mg/mL) | pH | SEC (% monomer) |
|---|---|---|---|
| Severe condition (40° C., 2 weeks) | 8.15 | 7.15 | 78.13 |
| Severe condition (40° C., 4 weeks) | 8.12 | 7.05 | 65.00 |

As a result of the stability test, the formulation candidate exhibited a stable state under the condition of −70° C., 5° C., and 25° C. From this result, the final formulation for GI-101 was determined to be 8 mg/mL of GI-101, 20 mM of histidine buffer (pH 7.0), 0.07 w/w % of poloxamer 188, 15 mg/mL of arginine-HCl and 150 mg/mL of sucrose.

TABLE 8

| Substance | Target concentration | Range |
|---|---|---|
| GI-101 | 8 mg/mL | 7.2 to 8.8 mg/mL |
| Buffer | histidine buffer: 20 mM | N/A |
| pH | pH 7.0 | pH 6.8 to 7.2 |
| Surfactant | poloxamer 188: 0.07 w/w % | 0.065 to 0.075 w/w % |
| Amino acid | arginine-HCl: 15 mg/mL | 14 to 16 mg/mL |
| Sugar | sucrose: 150 mg/mL | 140 to 160 mg/mL |

Example 3. Polysorbate 80 Addition Test

In the process of producing the GI-101 raw material medicine using the formulation candidate determined in Example 2.3., visible particles were found, and a formulation was additionally developed. It was identified that visible particles appear when silicone present in the raw material medicine binds to protein by physical stress to form a silicone-protein complex. Since there is a limit to removing silicone or alleviating physical stress in the process of producing the raw material medicine, a new formulation that inhibits the formation of a silicone-protein complex was developed to solve the problem. It has been reported that poloxamer 188 is an inefficient surfactant for inhibiting the formation of a silicone-protein complex, and based on this, an experiment was performed to add polysorbate 80 (PS80) as a surfactant.

Specifically, the test was performed by adding polysorbate 80 by concentrations (0 w/w %, 0.02 w/w %, 0.04 w/w %, 0.06 w/w %, 0.08 w/w %, and 0.1 w/w %) to GI-101 DS (4 mg/mL of GI-101, 20 mM of histidine buffer (pH 7.0), 0.07 w/w % of poloxamer 188, 15 mg/mL of arginine-HCl, and 150 mg/mL of sucrose). The concentration of GI-101 was adjusted to 4 mg/mL in order to increase long-term stability.

Example 3.1. Visual Particle Observation

Each of the three tubes was tested for each condition, and even when particles were observed only in one of the three tubes, it was labeled as 0 (i.e., 'particle observation') (Table 9).

TABLE 9

| Condition | | GI-101 DS + 0 w/w % PS80 | GI-101 DS + 0.02 w/w % PS80 | GI-101 DS + 0.04 w/w % PS80 | GI-101 DS + 0.06 w/w % PS80 | GI-101 DS + 0.08 w/w % PS80 | GI-101 DS + 0.1 w/w % PS80 | 8 mg/mL GI-101 w/o PS80 |
|---|---|---|---|---|---|---|---|---|
| Release time point (0 Time) | | X | X | X | X | X | X | X |
| Physical stress (continuous) | | ○ | not tested | not tested | not tested | not tested | not tested | ○ |
| Week 1 | physical stress | X | X | X | X | X | X | not tested |
| | storage at 5° C. | X | X | X | X | X | X | not tested |
| | storage at 25° C. | X | X | X | X | X | X | not tested |
| Week 2 | physical stress | X | X | X | X | X | X | not tested |
| | storage at 5° C. | X | X | X | X | X | X | not tested |
| | storage at 25° C. | X | X | X | X | X | X | not tested |
| Week 3 | physical stress | ○ | X | ○ | X | X | X | not tested |
| | storage at 5° C. | ○ | X | ○ | X | X | X | not tested |
| | storage at 25° C. | ○ | ○ | ○ | ○ | X | X | not tested |
| Week 4 | physical stress | not tested | not tested | not tested | not tested | X | X | not tested |
| | storage at 5° C. | not tested | not tested | not tested | not tested | X | X | not tested |
| | storage at 25° C. | not tested | not tested | not tested | not tested | X | X | not tested |

In the samples to which 0.08 w/w % or more of PS80 was added, no particles were observed until 4 weeks. In the case of a sample in which particles were observed at Week 3, the experiment at Week 4 was not performed.

Example 3.2. Evaluation of Quality Effect

In order to investigate the quality effect of the addition of polysorbate 80 (PS80), the protein concentration, charge variation, and purity of the sample to which 0.1 w/w % PS80 was added were measured. As a result of observing the sample to which 0.1 w/w % PS80 was added for up to 4 weeks, it was identified that the quality was maintained. The measurement results for each condition are shown in Table 10.

Considering that the addition of PS80 at a high concentration is effective in reducing visible particles, the concentration of PS80 was determined to be 0.1 w/w %. By combining these results, the final formulation composition for GI-101 was determined as shown in Table 11 below.

TABLE 11

| Substance | Target concentration | Range |
|---|---|---|
| GI-101 | 4 mg/mL | 3.6 to 4.4 mg/mL |
| Buffer | histidine buffer: 20 mM | N/A |
| pH | pH 7.0 | pH 6.8 to 7.2 |
| Surfactant | poloxamer 188: 0.07 w/w % | 0.065 to 0.075 w/w % |
| | polysorbate 80: 0.1 w/w % | 0.09 to 0.11 w/w % |
| Amino acid | arginine-HCl: 15 mg/mL | 14 to 16 mg/mL |
| Sugar | sucrose: 150 mg/mL | 140 to 160 mg/mL |

TABLE 10

| Analysis tool | | Unit | GI-101 DS + 0.1 w/w % PS80 0T | GI-101 DS + 0.1 w/w % PS80 physical stress | GI-101 DS + 0.1 w/w % PS80 5° C., 4 weeks | GI-101 DS + 0.1 w/w % PS80 25° C., 4 weeks |
|---|---|---|---|---|---|---|
| A280 (protein amount) | | mg/mL | 4.23 | 4.22 | 4.21 | 4.23 |
| icIEF | Peak 1 - Information only | Area % | 11.88 (pI: 5.32) | 11.21 (pI: 5.31) | 11.19 (pI: 5.32) | 12.11 (pI: 5.32) |
| | Peak 2 - Information only | Area % | 23.99 (pI: 5.48) | 25.21 (pI: 5.50) | 24.53 (pI: 5.50) | 26.77 (pI: 5.48) |
| | Peak 3 - Information only | Area % | 64.13 (pI: 5.62) | 63.58 (pI: 5.63) | 64.28 (pI: 5.60) | 61.13 (pI: 5.60) |
| SE-HPLC | HMWS | % | 1.43 | 1.66 | 1.63 | 1.39 |
| | Monomer | % | 98.2 | 97.96 | 97.97 | 97.9 |
| | LMWS | % | 0.37 | 0.38 | 0.4 | 0.71 |

The invention claimed is:

1. A pharmaceutical formulation comprising:
   (i) a fusion protein dimer comprising an IL-2 variant and a CD80 fragment at a concentration of 3.0 mg/mL to 5.0 mg/mL;
   (ii) a buffer at a concentration of 10 mM to 30 mM; and
   (iii) a surfactant at a concentration of 0.155 w/w % to 0.185 w/w %;
   wherein, the pH of the formulation is from 6.5 to 7.5,
   wherein the IL-2 variant is a peptide of SEQ ID NO: 10 with modifications, said modifications consisting of substitutions of the $38^{th}$ and $42^{nd}$ amino acids, the $38^{th}$, $42^{nd}$ and $45^{th}$ amino acids, $38^{th}$, $42^{nd}$ and $61^{st}$ amino acids, or $38^{th}$, $42^{nd}$ and $72^{nd}$ amino acids in the amino acid sequence of SEQ ID NO: 10 with another amino acid, and
   wherein the CD80 fragment is a protein composed of the $35^{th}$ to $242^{nd}$ amino acid residues in SEQ ID NO: 11.

2. The pharmaceutical formulation of claim 1, wherein the fusion protein dimer is at a concentration of 3.6 mg/mL to 4.4 mg/mL.

3. The pharmaceutical formulation of claim 1, wherein the buffer is histidine.

4. The pharmaceutical formulation of claim 3, wherein the histidine is at a concentration of 20 mM.

5. The pharmaceutical formulation of claim 1, wherein the pH of formulation is from 6.8 to 7.2.

6. The pharmaceutical formulation of claim 5, wherein the pH of the formulation is 7.0.

7. The pharmaceutical formulation of claim 1, wherein the surfactant is two surfactants selected from the group consisting of polysorbate 20, polysorbate 28, polysorbate 40, polysorbate 60, polysorbate 65, polysorbate 80, polysorbate 81, polysorbate 85, poloxamer 181, poloxamer 188, poloxamer 407, and polyethylene glycol (PEG).

8. The pharmaceutical formulation of claim 7, wherein the two surfactants are poloxamer 188 and polysorbate 80.

9. The pharmaceutical formulation of claim 8,
   wherein the poloxamer 188 is at a concentration of 0.065 w/w % to 0.075 w/w %, and
   the polysorbate 80 is at a concentration of 0.09 w/w % to 0.11 w/w %.

10. The pharmaceutical formulation of claim 1, wherein the pharmaceutical formulation further comprises an amino acid.

11. The pharmaceutical formulation of claim 10, wherein the amino acid is any one selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine and tryptophan.

12. The pharmaceutical formulation of claim 11, wherein the amino acid is arginine.

13. The pharmaceutical formulation of claim 10, wherein the amino acid is at a concentration of 10 mg/mL to 30 mg/mL.

14. The pharmaceutical formulation of claim 13, wherein the amino acid is at a concentration of 14 mg/mL to 16 mg/mL.

15. The pharmaceutical formulation of claim 14, wherein the amino acid is at a concentration of 15 mg/mL.

16. The pharmaceutical formulation of claim 1, wherein the pharmaceutical formulation further comprises a sugar.

17. The pharmaceutical formulation of claim 16, wherein the sugar is any one selected from the group consisting of sucrose, sorbitol, glycerol, trehalose and mannitol.

18. The pharmaceutical formulation of claim 16, wherein the sugar is at a concentration of 120 mg/mL to 180 mg/mL.

19. The pharmaceutical formulation of claim 18, wherein the sugar is at a concentration of 140 mg/mL to 160 mg/mL.

20. The pharmaceutical formulation of claim 17, wherein the sugar is sucrose.

21. The pharmaceutical formulation of claim 20, wherein the sucrose is at a concentration of 150 mg/mL.

22. A pharmaceutical formulation comprising:
   (i) a fusion protein dimer comprising an IL-2 variant and a CD80 fragment at a concentration of 3.0 mg/mL to 5.0 mg/mL;
   (ii) histidine at a concentration of 10 mM to 30 mM;
   (iii) poloxamer 188 at a concentration of 0.065 w/w % to 0.075 w/w %;
   (iv) polysorbate 80 at a concentration of 0.09 w/w % to 0.11 w/w %;
   (v) arginine at a concentration of 10 mg/mL to 30 mg/mL; and
   (vi) sucrose at a concentration of 120 mg/mL to 180 mg/mL,
   wherein, the pH of the formulation is from 6.5 to 7.5,
   wherein the IL-2 variant is a peptide of SEQ ID NO: 10 with modifications, said modifications consisting of substitutions of the $38^{th}$ and $42^{nd}$ amino acids, the $38^{th}$, $42^{nd}$ and $45^{th}$ amino acids, $38^{th}$, $42^{nd}$ and $61^{st}$ amino acids, or $38^{th}$, $42^{nd}$ and $72^{nd}$ amino acids in the amino acid sequence of SEQ ID NO: 10 with another amino acid, and
   wherein the CD80 fragment is a protein composed of the $35^{th}$ to $242^{nd}$ amino acid residues in SEQ ID NO: 11.

23. The pharmaceutical formulation of claim 22, wherein the formulation is an intravenous administration formulation.

* * * * *

SEQUENCE LISTING

<160> NUMBER OF SEQ ID NOS: 38

<210> SEQ ID NO 1
<211> LENGTH: 25
<212> TYPE: PRT
<213> ORGANISM: Artificial Sequence
<220> FEATURE:
<223> OTHER INFORMATION: signal peptide (TPA)

<400> SEQUENCE: 1

Met Asp Ala Met Leu Arg Gly Leu Cys Cys Val Leu Leu Leu Cys Gly
1               5                   10                  15

Ala Val Phe Val Ser Pro Ser His Ala
            20                  25

<210> SEQ ID NO 2
<211> LENGTH: 208
<212> TYPE: PRT
<213> ORGANISM: Artificial Sequence
<220> FEATURE:
<223> OTHER INFORMATION: hB7-1:35-242

<400> SEQUENCE: 2

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
                100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
        130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
                180                 185                 190

Gln Thr Phe Asn Trp Asn Thr Thr Lys Gln Glu His Phe Pro Asp Asn
        195                 200                 205

<210> SEQ ID NO 3
<211> LENGTH: 30
<212> TYPE: PRT
<213> ORGANISM: Artificial Sequence
<220> FEATURE:
<223> OTHER INFORMATION: hinge with linker

<400> SEQUENCE: 3

Gly Ser Gly Gly Gly Gly Ser Gly Gly Gly Gly Ser Gly Gly Gly Gly
1               5                   10                  15

```
Ser Ala Glu Ser Lys Tyr Gly Pro Pro Cys Pro Pro Cys Pro
            20              25              30
```

<210> SEQ ID NO 4
<211> LENGTH: 216
<212> TYPE: PRT
<213> ORGANISM: Artificial Sequence
<220> FEATURE:
<223> OTHER INFORMATION: immunoglobulin fc

<400> SEQUENCE: 4

```
Ala Pro Glu Ala Ala Gly Gly Pro Ser Val Phe Leu Phe Pro Pro Lys
1               5               10              15

Pro Lys Asp Gln Leu Met Ile Ser Arg Thr Pro Glu Val Thr Cys Val
            20              25              30

Val Val Asp Val Ser Gln Glu Asp Pro Glu Val Gln Phe Asn Trp Tyr
            35              40              45

Val Asp Gly Val Glu Val His Asn Ala Lys Thr Lys Pro Arg Glu Glu
        50              55              60

Gln Phe Asn Ser Thr Tyr Arg Val Val Ser Val Leu Thr Val Leu His
65              70              75              80

Gln Asp Trp Leu Asn Gly Lys Glu Tyr Lys Cys Lys Val Ser Asn Lys
                85              90              95

Gly Leu Pro Ser Ser Ile Glu Lys Thr Ile Ser Lys Ala Lys Gly Gln
            100             105             110

Pro Arg Glu Pro Gln Val Tyr Thr Leu Pro Pro Ser Gln Glu Glu Met
            115             120             125

Thr Lys Asn Gln Val Ser Leu Thr Cys Leu Val Lys Gly Phe Tyr Pro
        130             135             140

Ser Asp Ile Ala Val Glu Trp Glu Ser Asn Gly Gln Pro Glu Asn Asn
145             150             155             160

Tyr Lys Thr Thr Pro Pro Val Leu Asp Ser Asp Gly Ser Phe Phe Leu
                165             170             175

Tyr Ser Arg Leu Thr Val Asp Lys Ser Arg Trp Gln Glu Gly Asn Val
            180             185             190

Phe Ser Cys Ser Val Leu His Glu Ala Leu His Asn His Tyr Thr Gln
            195             200             205

Lys Ser Leu Ser Leu Ser Leu Gly
    210             215
```

<210> SEQ ID NO 5
<211> LENGTH: 5
<212> TYPE: PRT
<213> ORGANISM: Artificial Sequence
<220> FEATURE:
<223> OTHER INFORMATION: linker

<400> SEQUENCE: 5

```
Gly Gly Gly Gly Ser
1               5
```

<210> SEQ ID NO 6
<211> LENGTH: 133
<212> TYPE: PRT
<213> ORGANISM: Artificial Sequence
<220> FEATURE:
<223> OTHER INFORMATION: hIL-2M

<400> SEQUENCE: 6

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130
```

```
<210> SEQ ID NO 7
<211> LENGTH: 617
<212> TYPE: PRT
<213> ORGANISM: Artificial Sequence
<220> FEATURE:
<223> OTHER INFORMATION: fusion protein comprising variants of IL-2 and
      fragments of CD80

<400> SEQUENCE: 7

Met Asp Ala Met Leu Arg Gly Leu Cys Cys Val Leu Leu Leu Cys Gly
1               5                   10                  15

Ala Val Phe Val Ser Pro Ser His Ala Val Ile His Val Thr Lys Glu
            20                  25                  30

Val Lys Glu Val Ala Thr Leu Ser Cys Gly His Asn Val Ser Val Glu
        35                  40                  45

Glu Leu Ala Gln Thr Arg Ile Tyr Trp Gln Lys Glu Lys Lys Met Val
    50                  55                  60

Leu Thr Met Met Ser Gly Asp Met Asn Ile Trp Pro Glu Tyr Lys Asn
65                  70                  75                  80

Arg Thr Ile Phe Asp Ile Thr Asn Asn Leu Ser Ile Val Ile Leu Ala
                85                  90                  95

Leu Arg Pro Ser Asp Glu Gly Thr Tyr Glu Cys Val Val Leu Lys Tyr
            100                 105                 110

Glu Lys Asp Ala Phe Lys Arg Glu His Leu Ala Glu Val Thr Leu Ser
            115                 120                 125

Val Lys Ala Asp Phe Pro Thr Pro Ser Ile Ser Asp Phe Glu Ile Pro
    130                 135                 140

Thr Ser Asn Ile Arg Arg Ile Ile Cys Ser Thr Ser Gly Gly Phe Pro
145                 150                 155                 160

Glu Pro His Leu Ser Trp Leu Glu Asn Gly Glu Glu Leu Asn Ala Ile
            165                 170                 175

Asn Thr Thr Val Ser Gln Asp Pro Glu Thr Glu Leu Tyr Ala Val Ser
            180                 185                 190

Ser Lys Leu Asp Phe Asn Met Thr Thr Asn His Ser Phe Met Cys Leu
        195                 200                 205

Ile Lys Tyr Gly His Leu Arg Val Asn Gln Thr Phe Asn Trp Asn Thr
    210                 215                 220
```

-continued

```
Thr Lys Gln Glu His Phe Pro Asp Asn Gly Ser Gly Gly Gly Ser
225                 230                 235                 240

Gly Gly Gly Gly Ser Gly Gly Gly Ser Ala Glu Ser Lys Tyr Gly
                245                 250                 255

Pro Pro Cys Pro Pro Cys Pro Ala Pro Glu Ala Ala Gly Gly Pro Ser
            260             265             270

Val Phe Leu Phe Pro Pro Lys Pro Lys Asp Gln Leu Met Ile Ser Arg
        275             280             285

Thr Pro Glu Val Thr Cys Val Val Val Asp Val Ser Gln Glu Asp Pro
        290             295             300

Glu Val Gln Phe Asn Trp Tyr Val Asp Gly Val Glu Val His Asn Ala
305             310             315             320

Lys Thr Lys Pro Arg Glu Glu Gln Phe Asn Ser Thr Tyr Arg Val Val
            325             330             335

Ser Val Leu Thr Val Leu His Gln Asp Trp Leu Asn Gly Lys Glu Tyr
            340             345             350

Lys Cys Lys Val Ser Asn Lys Gly Leu Pro Ser Ser Ile Glu Lys Thr
            355             360             365

Ile Ser Lys Ala Lys Gly Gln Pro Arg Glu Pro Gln Val Tyr Thr Leu
        370             375             380

Pro Pro Ser Gln Glu Glu Met Thr Lys Asn Gln Val Ser Leu Thr Cys
385             390             395             400

Leu Val Lys Gly Phe Tyr Pro Ser Asp Ile Ala Val Glu Trp Glu Ser
            405             410             415

Asn Gly Gln Pro Glu Asn Asn Tyr Lys Thr Thr Pro Pro Val Leu Asp
            420             425             430

Ser Asp Gly Ser Phe Phe Leu Tyr Ser Arg Leu Thr Val Asp Lys Ser
            435             440             445

Arg Trp Gln Glu Gly Asn Val Phe Ser Cys Ser Val Leu His Glu Ala
        450             455             460

Leu His Asn His Tyr Thr Gln Lys Ser Leu Ser Leu Ser Leu Gly Gly
465             470             475             480

Gly Gly Gly Ser Ala Pro Thr Ser Ser Ser Thr Lys Lys Thr Gln Leu
            485             490             495

Gln Leu Glu His Leu Leu Leu Asp Leu Gln Met Ile Leu Asn Gly Ile
            500             505             510

Asn Asn Tyr Lys Asn Pro Lys Leu Thr Ala Met Leu Thr Ala Lys Phe
            515             520             525

Tyr Met Pro Lys Lys Ala Thr Glu Leu Lys His Leu Gln Cys Leu Glu
        530             535             540

Glu Glu Leu Lys Pro Leu Glu Glu Val Leu Asn Leu Ala Gln Ser Lys
545             550             555             560

Asn Phe His Leu Arg Pro Arg Asp Leu Ile Ser Asn Ile Asn Val Ile
            565             570             575

Val Leu Glu Leu Lys Gly Ser Glu Thr Thr Phe Met Cys Glu Tyr Ala
            580             585             590

Asp Glu Thr Ala Thr Ile Val Glu Phe Leu Asn Arg Trp Ile Thr Phe
            595             600             605

Cys Gln Ser Ile Ile Ser Thr Leu Thr
        610             615
```

<210> SEQ ID NO 8
<211> LENGTH: 1857

<212> TYPE: DNA
<213> ORGANISM: Artificial Sequence
<220> FEATURE:
<223> OTHER INFORMATION: nucleotiedes coding fusion protein (GI101)

<400> SEQUENCE: 8

```
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc     120 tgcggccaca acgtttcagt ggaagaactg gcccagacca ggatctactg gcagaaagaa     180
aagaaaatgg tgctgaccat gatgtccggc gacatgaaca tctggcctga gtacaagaac     240
cggaccatct tcgacatcac caacaacctg tccatcgtga ttctggccct gaggccttct     300
gatgagggca cctatgagtg cgtggtgctg aagtacgaga aggacgcctt caagcgcgag     360
cacctggctg aagtgacact gtccgtgaag gccgactttc ccacaccttc catctccgac     420
ttcgagatcc ctacctccaa catccggcgg atcatctgtt ctacctctgg cggctttcct     480
gagcctcacc tgtcttggct ggaaaacggc gaggaactga cgccatcaa caccaccgtg     540 tctcaggacc ccgaaaccga gctgtacgct gtgtcctcca gctggactt caacatgacc     600 accaaccaca gcttcatgtg cctgattaag tacggccacc tgagagtgaa ccagaccttc     660
aactggaaca ccaccaagca agagcacttc cctgacaatg gatctggcgg cggaggttct     720
ggcggaggtg gaagcggagg cggaggatct gctgagtcta gtatggccc tccttgtcct     780 ccatgtcctg ctccagaagc tgctggcgga ccctctgtgt tcctgtttcc tccaaagcct     840
aaggaccagc tcatgatctc tcggacaccc gaagtgacct gcgtggtggt ggatgtgtct     900
caagaggacc ctgaggtgca gttcaattgg tacgtggacg gcgtggaagt gcacaacgcc     960
aagaccaagc ctagagagga acagttcaac tccacctaca gagtggtgtc cgtgctgacc    1020
gtgctgcacc aggattggct gaacggcaaa gagtacaagt gcaaggtgtc caacaagggc    1080
ctgccttcca gcatcgaaaa gaccatctcc aaggctaagg gccagcctag ggaaccccag    1140
gtttacaccc tgcctccaag ccaagaggaa atgaccaaga ccaggtgtc cctgacctgc    1200 ctggtcaagg gcttctaccc ttccgacatt gccgtggaat gggagtccaa tggccagcct    1260
gagaacaact acaagaccac acctcctgtg ctggactccg acggctcctt ctttctgtac    1320
tctcgcctga ccgtggacaa gtctagatgg caagagggca cgtgttctc ctgctctgtg    1380 ctgcacgagg ccctgcacaa tcactacacc cagaagtccc tgtctctgtc tcttggaggt    1440
ggtggcggtt ctgcccctac cagctcctct accaagaaaa cccagctcca gttggagcat    1500
ctgctgctgg acctccagat gattctgaac gggatcaaca ctataagaa ccccaagctg    1560 accgccatgc tgaccgctaa gttctacatg cccaagaagg ccaccgagct gaagcacctc    1620
cagtgcctgg aagaagaact gaagcccctg aagaggtgc tgaatctggc ccagtccaag    1680
aacttccacc tgaggccacg ggacctgatc agcaacatca cgtgatcgt gctggaactg    1740 aagggctccg agacaacctt tatgtgcgag tacgccgacg agacagccac catcgtggaa    1800
tttctgaacc ggtggatcac cttctgccag agcatcatct ccacactgac ctgatga     1857
```

<210> SEQ ID NO 9
<211> LENGTH: 592
<212> TYPE: PRT
<213> ORGANISM: Artificial Sequence
<220> FEATURE:
<223> OTHER INFORMATION: fusion protein (GI101)

<400> SEQUENCE: 9

-continued

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
```

```
                420             425             430

Cys Ser Val Leu His Glu Ala Leu His Asn His Tyr Thr Gln Lys Ser
        435             440             445

Leu Ser Leu Ser Leu Gly Gly Gly Gly Ser Ala Pro Thr Ser Ser
        450             455             460

Ser Thr Lys Lys Thr Gln Leu Gln Leu Glu His Leu Leu Leu Asp Leu
465             470             475             480

Gln Met Ile Leu Asn Gly Ile Asn Asn Tyr Lys Asn Pro Lys Leu Thr
                485             490             495

Ala Met Leu Thr Ala Lys Phe Tyr Met Pro Lys Lys Ala Thr Glu Leu
                500             505             510

Lys His Leu Gln Cys Leu Glu Glu Glu Leu Lys Pro Leu Glu Glu Val
        515             520             525

Leu Asn Leu Ala Gln Ser Lys Asn Phe His Leu Arg Pro Arg Asp Leu
        530             535             540

Ile Ser Asn Ile Asn Val Ile Val Leu Glu Leu Lys Gly Ser Glu Thr
545             550             555             560

Thr Phe Met Cys Glu Tyr Ala Asp Glu Thr Ala Thr Ile Val Glu Phe
                565             570             575

Leu Asn Arg Trp Ile Thr Phe Cys Gln Ser Ile Ile Ser Thr Leu Thr
        580             585             590
```

```
<210> SEQ ID NO 10
<211> LENGTH: 133
<212> TYPE: PRT
<213> ORGANISM: Artificial Sequence
<220> FEATURE:
<223> OTHER INFORMATION: hIL-2

<400> SEQUENCE: 10

Ala Pro Thr Ser Ser Ser Thr Lys Lys Thr Gln Leu Gln Leu Glu His
1               5               10              15

Leu Leu Leu Asp Leu Gln Met Ile Leu Asn Gly Ile Asn Asn Tyr Lys
                20              25              30

Asn Pro Lys Leu Thr Arg Met Leu Thr Phe Lys Phe Tyr Met Pro Lys
        35              40              45

Lys Ala Thr Glu Leu Lys His Leu Gln Cys Leu Glu Glu Glu Leu Lys
        50              55              60

Pro Leu Glu Glu Val Leu Asn Leu Ala Gln Ser Lys Asn Phe His Leu
65              70              75              80

Arg Pro Arg Asp Leu Ile Ser Asn Ile Asn Val Ile Val Leu Glu Leu
                85              90              95

Lys Gly Ser Glu Thr Thr Phe Met Cys Glu Tyr Ala Asp Glu Thr Ala
                100             105             110

Thr Ile Val Glu Phe Leu Asn Arg Trp Ile Thr Phe Cys Gln Ser Ile
        115             120             125

Ile Ser Thr Leu Thr
        130
```

```
<210> SEQ ID NO 11
<211> LENGTH: 288
<212> TYPE: PRT
<213> ORGANISM: Artificial Sequence
<220> FEATURE:
<223> OTHER INFORMATION: CD80

<400> SEQUENCE: 11
```

-continued

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
        130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
            245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285
```

```
<210> SEQ ID NO 12
<211> LENGTH: 215
<212> TYPE: PRT
<213> ORGANISM: Artificial Sequence
<220> FEATURE:
<223> OTHER INFORMATION: modified Fc

<400> SEQUENCE: 12

Ser His Thr Gln Pro Leu Gly Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80
```

```
Trp Leu Asn Gly Lys Glu Tyr Lys Cys Lys Val Ser Asn Lys Gly Leu
                85              90              95

Pro Ser Ser Ile Glu Lys Thr Ile Ser Lys Ala Lys Gly Gln Pro Arg
                100             105             110

Glu Pro Gln Val Tyr Thr Leu Pro Pro Ser Gln Glu Glu Met Thr Lys
                115             120             125

Asn Gln Val Ser Leu Thr Cys Leu Val Lys Gly Phe Tyr Pro Ser Asp
        130             135             140

Ile Ala Val Glu Trp Glu Ser Asn Gly Gln Pro Glu Asn Asn Tyr Lys
145             150             155             160

Thr Thr Pro Pro Val Leu Asp Ser Asp Gly Ser Phe Phe Leu Tyr Ser
                165             170             175

Arg Leu Thr Val Asp Lys Ser Arg Trp Gln Glu Gly Asn Val Phe Ser
                180             185             190

Cys Ser Val Met His Glu Ala Leu His Asn His Tyr Thr Gln Lys Ser
                195             200             205

Leu Ser Leu Ser Leu Gly Lys
        210             215
```

```
<210> SEQ ID NO 13
<211> LENGTH: 306
<212> TYPE: PRT
<213> ORGANISM: Artificial Sequence
<220> FEATURE:
<223> OTHER INFORMATION: mCD80

<400> SEQUENCE: 13
```

```
Met Ala Cys Asn Cys Gln Leu Met Gln Asp Thr Pro Leu Leu Lys Phe
1               5               10              15

Pro Cys Pro Arg Leu Ile Leu Leu Phe Val Leu Leu Ile Arg Leu Ser
                20              25              30

Gln Val Ser Ser Asp Val Asp Glu Gln Leu Ser Lys Ser Val Lys Asp
        35              40              45

Lys Val Leu Leu Pro Cys Arg Tyr Asn Ser Pro His Glu Asp Glu Ser
        50              55              60

Glu Asp Arg Ile Tyr Trp Gln Lys His Asp Lys Val Val Leu Ser Val
65              70              75              80

Ile Ala Gly Lys Leu Lys Val Trp Pro Glu Tyr Lys Asn Arg Thr Leu
                85              90              95

Tyr Asp Asn Thr Thr Tyr Ser Leu Ile Ile Leu Gly Leu Val Leu Ser
                100             105             110

Asp Arg Gly Thr Tyr Ser Cys Val Val Gln Lys Lys Glu Arg Gly Thr
                115             120             125

Tyr Glu Val Lys His Leu Ala Leu Val Lys Leu Ser Ile Lys Ala Asp
        130             135             140

Phe Ser Thr Pro Asn Ile Thr Glu Ser Gly Asn Pro Ser Ala Asp Thr
145             150             155             160

Lys Arg Ile Thr Cys Phe Ala Ser Gly Gly Phe Pro Lys Pro Arg Phe
                165             170             175

Ser Trp Leu Glu Asn Gly Arg Glu Leu Pro Gly Ile Asn Thr Thr Ile
                180             185             190

Ser Gln Asp Pro Glu Ser Glu Leu Tyr Thr Ile Ser Ser Gln Leu Asp
                195             200             205

Phe Asn Thr Thr Arg Asn His Thr Ile Lys Cys Leu Ile Lys Tyr Gly
        210             215             220
```

```
Asp Ala His Val Ser Glu Asp Phe Thr Trp Glu Lys Pro Pro Glu Asp
225             230             235             240

Pro Pro Asp Ser Lys Asn Thr Leu Val Leu Phe Gly Ala Gly Phe Gly
            245             250             255

Ala Val Ile Thr Val Val Val Ile Val Val Ile Ile Lys Cys Phe Cys
            260             265             270

Lys His Arg Ser Cys Phe Arg Arg Asn Glu Ala Ser Arg Glu Thr Asn
        275             280             285

Asn Ser Leu Thr Phe Gly Pro Glu Glu Ala Leu Ala Glu Gln Thr Val
    290             295             300

Phe Leu
305
```

```
<210> SEQ ID NO 14
<211> LENGTH: 1848
<212> TYPE: DNA
<213> ORGANISM: Artificial Sequence
<220> FEATURE:
<223> OTHER INFORMATION: nucleotiedes coding fusion protein (mGI101)

<400> SEQUENCE: 14
atggatgcta tgctgagagg cctgtgttgc gtgctgctgc tgtgtggcgc tgtgttcgtg      60
tctccttctc acgctgtgga cgagcagctc tccaagtccg tgaaggataa ggtcctgctg     120
ccttgccggt acaactctcc tcacgaggac gagtctgagg accggatcta ctggcagaaa     180
cacgacaagg tggtgctgtc cgtgatcgcc ggaaagctga agtgtggcc tgagtacaag      240 aacaggaccc tgtacgacaa caccacctac agcctgatca tcctgggcct cgtgctgagc     300
gatagaggca cctattcttg cgtggtgcag aagaaagagc ggggcaccta cgaagtgaag     360
cacctggctc tggtcaagct gtccatcaag gccgacttca gcacccctaa catcaccgag     420
tctggcaacc cttccgccga caccaagaga atcacctgtt cgcctctgg cggcttccct       480 aagcctcggt tctcttggct ggaaaacggc agagagctgc ccggcatcaa taccaccatt     540
tctcaggacc agagtccga gctgtacacc atctccagcc agctcgactt taacaccacc      600
agaaaccaca ccatcaagtg cctgattaag tacggcgacg cccacgtgtc cgaggacttt     660
acttgggaga aacctcctga ggaccctcct gactctggat ctggcggcgg aggttctggc     720
ggaggtggaa gcggaggcgg aggatctgct gagtctaagt atggccctcc ttgtcctcca     780
tgtcctgctc agaagctgc tggcggaccc tctgtgttcc tgtttcctcc aaagcctaag     840
gaccagctca tgatctctcg gacccctgaa gtgacctgcg tggtggtgga tgtgtctcaa     900
gaggaccctg aggtgcagtt caattggtac gtggacggcg tggaagtgca caacgccaag     960
accaagccta gagaggaaca gttcaactcc acctatagag tggtgtccgt gctgaccgtg    1020
ctgcaccagg attggctgaa cggcaaagag tacaagtgca aggtgtccaa caagggcctg    1080
ccttccagca tcgaaaagac catcagcaag gctaagggcc agcctaggga accccaggtt    1140
tacaccctgc ctccaagcca agaggaaatg accaagaacc aggtgtccct gacctgcctg    1200
gtcaagggct cttacccttc cgacattgcc gtggaatggg agtccaatgg ccagcctgag    1260
aacaactaca gaccacacc tcctgtgctg gactccgacg gctccttctt tctgtactct    1320
cgcctgaccg tggacaagtc taggtggcaa gagggcaacg tgttctcctg ctctgtgctg    1380
cacgaggctc tgcacaacca ctacacccag aagtccctgt ctctgtctct ggaggtggt    1440 ggcggttctg cccctacctc cagctctacc aagaaaaccc agctccagtt ggagcatctg    1500
ctgctggacc tccagatgat cctgaatggc atcaacaatt acaagaaccc caagctgacc    1560
```

-continued

```
gccatgctga ccgctaagtt ctacatgccc aagaaggcca ccgagctgaa gcacttgcag      1620
tgcctggaag aggaactgaa gcccctggaa gaagtgctga atctggccca gtccaagaac      1680
ttccacctga ggcctaggga cctgatctcc aacatcaacg tgatcgtgct ggaactgaaa      1740
ggctccgaga caaccttcat gtgcgagtac gccgacgaga cagccaccat cgtggaattt      1800
ctgaaccggt ggatcacctt ctgccagagc atcatctcca cactgacc                  1848
```

<210> SEQ ID NO 15
<211> LENGTH: 616
<212> TYPE: PRT
<213> ORGANISM: Artificial Sequence
<220> FEATURE:
<223> OTHER INFORMATION: fusion protein (mGI101)

<400> SEQUENCE: 15

```
Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220

Pro Pro Glu Asp Pro Pro Asp Ser Gly Ser Gly Gly Gly Ser Gly
225                 230                 235                 240

Gly Gly Gly Ser Gly Gly Gly Ser Ala Glu Ser Lys Tyr Gly Pro
            245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
```

-continued

```
305             310             315             320

Thr Lys Pro Arg Glu Glu Gln Phe Asn Ser Thr Tyr Arg Val Val Ser
                325             330             335

Val Leu Thr Val Leu His Gln Asp Trp Leu Asn Gly Lys Glu Tyr Lys
            340             345             350

Cys Lys Val Ser Asn Lys Gly Leu Pro Ser Ser Ile Glu Lys Thr Ile
            355             360             365

Ser Lys Ala Lys Gly Gln Pro Arg Glu Pro Gln Val Tyr Thr Leu Pro
    370             375             380

Pro Ser Gln Glu Glu Met Thr Lys Asn Gln Val Ser Leu Thr Cys Leu
385             390             395             400

Val Lys Gly Phe Tyr Pro Ser Asp Ile Ala Val Glu Trp Glu Ser Asn
                405             410             415

Gly Gln Pro Glu Asn Asn Tyr Lys Thr Thr Pro Pro Val Leu Asp Ser
            420             425             430

Asp Gly Ser Phe Phe Leu Tyr Ser Arg Leu Thr Val Asp Lys Ser Arg
            435             440             445

Trp Gln Glu Gly Asn Val Phe Ser Cys Ser Val Leu His Glu Ala Leu
    450             455             460

His Asn His Tyr Thr Gln Lys Ser Leu Ser Leu Ser Leu Gly Gly Gly
465             470             475             480

Gly Gly Ser Ala Pro Thr Ser Ser Ser Thr Lys Lys Thr Gln Leu Gln
            485             490             495

Leu Glu His Leu Leu Leu Asp Leu Gln Met Ile Leu Asn Gly Ile Asn
            500             505             510

Asn Tyr Lys Asn Pro Lys Leu Thr Ala Met Leu Thr Ala Lys Phe Tyr
            515             520             525

Met Pro Lys Lys Ala Thr Glu Leu Lys His Leu Gln Cys Leu Glu Glu
    530             535             540

Glu Leu Lys Pro Leu Glu Glu Val Leu Asn Leu Ala Gln Ser Lys Asn
545             550             555             560

Phe His Leu Arg Pro Arg Asp Leu Ile Ser Asn Ile Asn Val Ile Val
            565             570             575

Leu Glu Leu Lys Gly Ser Glu Thr Thr Phe Met Cys Glu Tyr Ala Asp
            580             585             590

Glu Thr Ala Thr Ile Val Glu Phe Leu Asn Arg Trp Ile Thr Phe Cys
    595             600             605

Gln Ser Ile Ile Ser Thr Leu Thr
    610             615
```

```
<210> SEQ ID NO 16
<211> LENGTH: 1437
<212> TYPE: DNA
<213> ORGANISM: Artificial Sequence
<220> FEATURE:
<223> OTHER INFORMATION: nucleotiedes coding fusion protein (GI101C1)

<400> SEQUENCE: 16
atggatgcta tgctgagagg cctgtgttgc gtgctgctgc tgtgtggcgc tgtgttcgtg      60
tctccttctc acgctgtgat ccacgtgacc aaagaagtga aagaggtcgc cacactgtcc     120
tgcggccaca acgtttcagt ggaagaactg gcccagacca ggatctactg cagaaagaa      180 aagaaaatgg tgctgaccat gatgtccggc gacatgaaca tctggcctga gtacaagaac     240
cggaccatct tcgacatcac caacaacctg tccatcgtga ttctggccct gaggccttct     300
```

```
gatgagggca cctatgagtg cgtggtgctg aagtacgaga aggacgcctt caagcgcgag    360
cacctggctg aagtgacact gtccgtgaag gccgactttc ccacaccttc catctccgac    420
ttcgagatcc ctacctccaa catccggcgg atcatctgtt ctacctctgg cggctttcct    480
gagcctcacc tgtcttggct ggaaaacggc gaggaactga cgccatcaa caccaccgtg     540 tctcaggacc ccgaaaccga gctgtacgct gtgtcctcca agctggactt caacatgacc    600
accaaccaca gcttcatgtg cctgattaag tacggccacc tgagagtgaa ccagaccttc    660
aactggaaca ccaccaagca agagcacttc cctgacaatg gatctggcgg cggaggttct    720
ggcggaggtg gaagcggagg cggaggatct gctgagtcta gtatggccc tccttgtcct     780 ccatgtcctg ctccagaagc tgctggcgga ccctctgtgt tcctgtttcc tccaaagcct    840
aaggaccagc tcatgatctc tcggacaccc gaagtgacct gcgtggtggt ggatgtgtct    900
caagaggacc ctgaggtgca gttcaattgg tacgtggacg gcgtggaagt gcacaacgcc    960
aagaccaagc ctagagagga acagttcaac tccacctaca gagtggtgtc cgtgctgacc    1020
gtgctgcacc aggattggct gaacggcaaa gagtacaagt gcaaggtgtc caacaagggc    1080
ctgccttcca gcatcgaaaa gaccatctcc aaggctaagg gccagcctag ggaaccccag    1140
gtttacaccc tgcctccaag ccaagaggaa atgaccaaga ccaggtgtc cctgacctgc     1200 ctggtcaagg gcttctaccc ttccgacatt gccgtggaat gggagtccaa tggccagcct    1260
gagaacaact acaagaccac acctcctgtg ctggactccg acggctcctt ctttctgtac    1320
tctcgcctga ccgtggacaa gtctaggtgg caagagggca acgtgttctc ctgctctgtg    1380
ctgcacgagg ccctgcacaa tcactacacc cagaagtccc tgtctctgtc cctgggc      1437
```

```
<210> SEQ ID NO 17
<211> LENGTH: 454
<212> TYPE: PRT
<213> ORGANISM: Artificial Sequence
<220> FEATURE:
<223> OTHER INFORMATION: fusion protein (GI101C1)

<400> SEQUENCE: 17

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
```

```
                165              170              175

Asn His Ser Phe Met Cys Leu Ile Lys Tyr Gly His Leu Arg Val Asn
            180              185              190

Gln Thr Phe Asn Trp Asn Thr Thr Lys Gln Glu His Phe Pro Asp Asn
        195              200              205

Gly Ser Gly Gly Gly Gly Ser Gly Gly Gly Gly Ser Gly Gly Gly Gly
    210              215              220

Ser Ala Glu Ser Lys Tyr Gly Pro Pro Cys Pro Pro Cys Pro Ala Pro
225              230              235              240

Glu Ala Ala Gly Gly Pro Ser Val Phe Leu Phe Pro Pro Lys Pro Lys
            245              250              255

Asp Gln Leu Met Ile Ser Arg Thr Pro Glu Val Thr Cys Val Val Val
            260              265              270

Asp Val Ser Gln Glu Asp Pro Glu Val Gln Phe Asn Trp Tyr Val Asp
            275              280              285

Gly Val Glu Val His Asn Ala Lys Thr Lys Pro Arg Glu Glu Gln Phe
    290              295              300

Asn Ser Thr Tyr Arg Val Val Ser Val Leu Thr Val Leu His Gln Asp
305              310              315              320

Trp Leu Asn Gly Lys Glu Tyr Lys Cys Lys Val Ser Asn Lys Gly Leu
            325              330              335

Pro Ser Ser Ile Glu Lys Thr Ile Ser Lys Ala Lys Gly Gln Pro Arg
            340              345              350

Glu Pro Gln Val Tyr Thr Leu Pro Pro Ser Gln Glu Glu Met Thr Lys
            355              360              365

Asn Gln Val Ser Leu Thr Cys Leu Val Lys Gly Phe Tyr Pro Ser Asp
    370              375              380

Ile Ala Val Glu Trp Glu Ser Asn Gly Gln Pro Glu Asn Asn Tyr Lys
385              390              395              400

Thr Thr Pro Pro Val Leu Asp Ser Asp Gly Ser Phe Phe Leu Tyr Ser
            405              410              415

Arg Leu Thr Val Asp Lys Ser Arg Trp Gln Glu Gly Asn Val Phe Ser
            420              425              430

Cys Ser Val Leu His Glu Ala Leu His Asn His Tyr Thr Gln Lys Ser
            435              440              445

Leu Ser Leu Ser Leu Gly
    450
```

<210> SEQ ID NO 18
<211> LENGTH: 1176
<212> TYPE: DNA
<213> ORGANISM: Artificial Sequence
<220> FEATURE:
<223> OTHER INFORMATION: nucleotiedes coding fusion protein (GI101C2)

<400> SEQUENCE: 18

```
atggatgcta tgctgagagg cctgtgttgc gtgctgctgc tgtgtggcgc tgtgttcgtg     60
tctccatctc acgccgctga gtctaagtac ggccctcctt gtcctccatg tcctgctcca    120
gaagctgctg gcggaccctc tgtgttcctg tttcctccaa agcctaagga ccagctcatg    180
atctctcgga cccctgaagt gacctgcgtg gtggtggatg tgtctcaaga ggaccctgag    240
gtgcagttca attggtacgt ggacggcgtg gaagtgcaca cgccaagac caagcctaga    300 gaggaacagt tcaactccac ctacagagtg gtgtccgtgc tgaccgtgct gcaccaggat    360
tggctgaacg gcaaagagta caagtgcaag gtgtccaaca agggcctgcc ttccagcatc    420
```

-continued

```
gaaaagacca tctccaaggc taagggccag cctagggaac cccaggttta caccctgcct    480
ccaagccaag aggaaatgac caagaaccag gtgtccctga cctgcctggt caagggcttc    540
tacccttccg acattgccgt ggaatgggag tccaatggcc agcctgagaa caactacaag    600
accacacctc ctgtgctgga ctccgacggc tccttctttc tgtactctcg cctgaccgtg    660
gacaagtcta ggtggcaaga gggcaacgtg ttctcctgct ctgtgctgca cgaggccctg    720
cacaatcact acacccagaa gtccctgtct ctgtctcttg gcggaggcgg aggatctgct    780
cctacctcca gctccaccaa gaaaacccag ctccagttgg agcatctgct gctggacctc    840
cagatgatcc tgaatggcat caacaattac aagaacccca agctgaccgc catgctgacc    900
gctaagttct acatgcccaa gaaggccacc gagctgaagc acctccagtg cctggaagag    960
gaactgaagc ccctggaaga agtgctgaat ctggcccagt ccaagaactt ccacctgagg    1020
cctagggacc tgatctccaa catcaacgtg atcgtgctgg aactgaaagg ctccgagaca    1080
accttcatgt gcgagtacgc cgacgagaca gccaccatcg tggaatttct gaaccggtgg    1140
atcaccttct gccagtccat catctccaca ctgacc                             1176
```

<210> SEQ ID NO 19
<211> LENGTH: 367
<212> TYPE: PRT
<213> ORGANISM: Artificial Sequence
<220> FEATURE:
<223> OTHER INFORMATION: fusion protein (GI101C2)

<400> SEQUENCE: 19

```
Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Gln Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Leu His Glu Ala Leu His Asn His Tyr Thr Gln Lys Ser Leu
    210                 215                 220
```

```
Ser Leu Ser Leu Gly Gly Gly Gly Gly Ser Ala Pro Thr Ser Ser Ser
225             230                 235                 240

Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Ala
            260                 265                 270

Met Leu Thr Ala Lys Phe Tyr Met Pro Lys Lys Ala Thr Glu Leu Lys
        275                 280                 285

His Leu Gln Cys Leu Glu Glu Glu Leu Lys Pro Leu Glu Glu Val Leu
    290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Cys Gln Ser Ile Ile Ser Thr Leu Thr
        355                 360                 365
```

```
<210> SEQ ID NO 20
<211> LENGTH: 1434
<212> TYPE: DNA
<213> ORGANISM: Artificial Sequence
<220> FEATURE:
<223> OTHER INFORMATION: nucleotiedes coding fusion protein (mGI101C1)

<400> SEQUENCE: 20
atggatgcta tgctgagagg cctgtgttgc gtgctgctgc tgtgtggcgc tgtgttcgtg      60
tctccttctc acgctgtgga cgagcagctc tccaagtccg tgaaggataa ggtcctgctg     120
ccttgccggt acaactctcc tcacgaggac gagtctgagg accggatcta ctggcagaaa     180
cacgacaagg tggtgctgtc cgtgatcgcc ggaaagctga aagtgtggcc tgagtacaag     240
aacaggaccc tgtacgacaa caccacctac agcctgatca tcctgggcct cgtgctgagc     300
gatagaggca cctattcttg cgtggtgcag aagaaagagc ggggcaccta cgaagtgaag     360
cacctggctc tggtcaagct gtccatcaag gccgacttca gcacccctaa catcaccgag     420
tctggcaacc cttccgccga caccaagaga atcacctgtt cgcctctgg cggcttccct      480 aagcctcggt tctcttggct ggaaacggc agagagctgc ccggcatcaa taccaccatt      540
tctcaggacc cagagtccga gctgtacacc atctccagcc agctcgactt taacaccacc     600
agaaaccaca ccatcaagtg cctgattaag tacggcgacg cccacgtgtc cgaggacttt     660
acttgggaga aacctcctga ggaccctcct gactctggat ctggcggcgg aggttctggc     720
ggaggtggaa gcggaggcgg aggatctgct gagtctaagt atggccctcc ttgtcctcca     780
tgtcctgctc agaagctgc tggcggaccc tctgtgttcc tgtttcctcc aaagcctaag     840
gaccagctca tgatctctcg gacccctgaa gtgacctgcg tggtggtgga tgtgtctcaa     900
gaggaccctg aggtgcagtt caattggtac gtggacggcg tggaagtgca caacgccaag     960
accaagccta gagaggaaca gttcaactcc acctatagag tggtgtccgt gctgaccgtg    1020
ctgcaccagg attggctgaa cggcaaagag tacaagtgca aggtgtccaa caagggcctg    1080
ccttccagca tcgaaaagac catcagcaag gctaagggcc agcctaggga accccaggtt    1140
tacaccctgc ctccaagcca agaggaaatg accaagaacc aggtgtccct gacctgcctg    1200
gtcaagggct ctacccttc cgacattgcc gtggaatggg agtccaatgg ccagcctgag    1260
```

```
aacaactaca agaccacacc tcctgtgctg gactccgacg gctccttctt tctgtactct    1320
cgcctgaccg tggacaagtc taggtggcaa gagggcaacg tgttctcctg ctctgtgctg    1380
cacgaggctc tgcacaacca ctacacccag aagtccctgt ctctgtccct gggc          1434
```

```
<210> SEQ ID NO 21
<211> LENGTH: 478
<212> TYPE: PRT
<213> ORGANISM: Artificial Sequence
<220> FEATURE:
<223> OTHER INFORMATION: fusion protein (mGI101C1)

<400> SEQUENCE: 21

Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
            115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220

Pro Pro Glu Asp Pro Pro Asp Ser Gly Ser Gly Gly Gly Ser Gly
225                 230                 235                 240

Gly Gly Gly Ser Gly Gly Gly Ser Ala Glu Ser Lys Tyr Gly Pro
            245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
            325                 330                 335
```

```
Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
            355                 360                 365

Ser Lys Ala Lys Gly Gln Pro Arg Glu Pro Gln Val Tyr Thr Leu Pro
    370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
            435                 440                 445

Trp Gln Glu Gly Asn Val Phe Ser Cys Ser Val Leu His Glu Ala Leu
    450                 455                 460

His Asn His Tyr Thr Gln Lys Ser Leu Ser Leu Ser Leu Gly
465                 470                 475

<210> SEQ ID NO 22
<211> LENGTH: 133
<212> TYPE: PRT
<213> ORGANISM: Artificial Sequence
<220> FEATURE:
<223> OTHER INFORMATION: variants of IL-2 (3M, M45)

<400> SEQUENCE: 22

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Ala Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130

<210> SEQ ID NO 23
<211> LENGTH: 133
<212> TYPE: PRT
<213> ORGANISM: Artificial Sequence
<220> FEATURE:
<223> OTHER INFORMATION: variants of IL-2 (3M, M61)

<400> SEQUENCE: 23

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30
```

Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Arg Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 24
<211> LENGTH: 133
<212> TYPE: PRT
<213> ORGANISM: Artificial Sequence
<220> FEATURE:
<223> OTHER INFORMATION: variants of IL-2 (3M, M72)

<400> SEQUENCE: 24

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
        20                  25                  30

Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Glu Glu Leu Lys
        50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 25
<211> LENGTH: 1851
<212> TYPE: DNA
<213> ORGANISM: Artificial Sequence
<220> FEATURE:
<223> OTHER INFORMATION: nucleotiedes coding fusion protein (GI102-M45)

<400> SEQUENCE: 25
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc      120 tgcggccaca acgtttcagt ggaagaactg gcccagacca ggatctactg gcagaaagaa      180
aagaaaatgg tgctgaccat gatgtccggc gacatgaaca tctggcctga gtacaagaac      240
cggaccatct tcgacatcac caacaacctg tccatcgtga ttctggccct gaggccttct      300

-continued

```
gatgagggca cctatgagtg cgtggtgctg aagtacgaga aggacgcctt caagcgcgag      360
cacctggctg aagtgacact gtccgtgaag gccgactttc ccacaccttc catctccgac      420
ttcgagatcc ctacctccaa catccggcgg atcatctgtt ctacctctgg cggctttcct      480
gagcctcacc tgtcttggct ggaaaacggc gaggaactga cgccatcaa caccaccgtg      540 tctcaggacc ccgaaaccga gctgtacgct gtgtcctcca agctggactt caacatgacc      600
accaaccaca gcttcatgtg cctgattaag tacggccacc tgagagtgaa ccagaccttc      660
aactggaaca ccaccaagca agagcacttc cctgacaatg gatctggcgg cggaggttct      720
ggcggaggtg gaagcggagg cggaggatct gctgagtcta agtatggccc tccttgtcct      780
ccatgtcctg ctccagaagc tgctggcgga ccctctgtgt tcctgtttcc tccaaagcct      840
aaggaccagc tcatgatctc tcggacaccc gaagtgacct gcgtggtggt ggatgtgtct      900
caagaggacc ctgaggtgca gttcaattgg tacgtggacg gcgtggaagt gcacaacgcc      960
aagaccaagc ctagagagga acagttcaac tccacctaca gagtggtgtc cgtgctgacc     1020
gtgctgcacc aggattggct gaacggcaaa gagtacaagt gcaaggtgtc caacaagggc     1080
ctgccttcca gcatcgaaaa gaccatctcc aaggctaagg gccagcctag ggaaccccag     1140
gtttacaccc tgcctccaag ccaagaggaa atgaccaaga ccaggtgtc cctgacctgc     1200 ctggtcaagg gcttctaccc ttccgacatt gccgtggaat gggagtccaa tggccagcct     1260
gagaacaact acaagaccac acctcctgtg ctggactccg acggctcctt ctttctgtac     1320
tctcgcctga ccgtggacaa gtctagatgg caagagggca cgtgttctc ctgctctgtg     1380 ctgcacgagg ccctgcacaa tcactacacc cagaagtccc tgtctctgtc tcttggaggt     1440
ggtggcggtt ctgcccctac cagctcctct accaagaaaa cccagctcca gttggagcat     1500
ctgctgctgg acctccagat gattctgaac gggatcaaca ctataagaa ccccaagctg     1560 accgccatgc tgaccgctaa gttcgccatg cccaagaagg ccaccgagct gaagcacctc     1620
cagtgcctga agaagaact gaagcccctg aagaggtgc tgaatctggc ccagtccaag     1680
aacttccacc tgaggccacg ggacctgatc agcaacatca cgtgatcgt gctggaactg     1740 aagggctccg agacaacctt tatgtgcgag tacgccgacg agacagccac catcgtggaa     1800
tttctgaacc ggtggatcac cttctgccag agcatcatct ccacactgac c              1851
```

<210> SEQ ID NO 26
<211> LENGTH: 592
<212> TYPE: PRT
<213> ORGANISM: Artificial Sequence
<220> FEATURE:
<223> OTHER INFORMATION: fusion protein (GI102-M45)

<400> SEQUENCE: 26

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95
```

-continued

```
Leu Ala Glu Val Thr Leu Ser Val Lys Ala Asp Phe Pro Thr Pro Ser
        100             105             110

Ile Ser Asp Phe Glu Ile Pro Thr Ser Asn Ile Arg Arg Ile Ile Cys
        115             120             125

Ser Thr Ser Gly Gly Phe Pro Glu Pro His Leu Ser Trp Leu Glu Asn
        130             135             140

Gly Glu Glu Leu Asn Ala Ile Asn Thr Thr Val Ser Gln Asp Pro Glu
145             150             155             160

Thr Glu Leu Tyr Ala Val Ser Ser Lys Leu Asp Phe Asn Met Thr Thr
                165             170             175

Asn His Ser Phe Met Cys Leu Ile Lys Tyr Gly His Leu Arg Val Asn
            180             185             190

Gln Thr Phe Asn Trp Asn Thr Thr Lys Gln Glu His Phe Pro Asp Asn
            195             200             205

Gly Ser Gly Gly Gly Gly Ser Gly Gly Gly Gly Ser Gly Gly Gly Gly
        210             215             220

Ser Ala Glu Ser Lys Tyr Gly Pro Pro Cys Pro Pro Cys Pro Ala Pro
225             230             235             240

Glu Ala Ala Gly Gly Pro Ser Val Phe Leu Phe Pro Pro Lys Pro Lys
                245             250             255

Asp Gln Leu Met Ile Ser Arg Thr Pro Glu Val Thr Cys Val Val Val
            260             265             270

Asp Val Ser Gln Glu Asp Pro Glu Val Gln Phe Asn Trp Tyr Val Asp
            275             280             285

Gly Val Glu Val His Asn Ala Lys Thr Lys Pro Arg Glu Glu Gln Phe
        290             295             300

Asn Ser Thr Tyr Arg Val Val Ser Val Leu Thr Val Leu His Gln Asp
305             310             315             320

Trp Leu Asn Gly Lys Glu Tyr Lys Cys Lys Val Ser Asn Lys Gly Leu
                325             330             335

Pro Ser Ser Ile Glu Lys Thr Ile Ser Lys Ala Lys Gly Gln Pro Arg
            340             345             350

Glu Pro Gln Val Tyr Thr Leu Pro Pro Ser Gln Glu Glu Met Thr Lys
            355             360             365

Asn Gln Val Ser Leu Thr Cys Leu Val Lys Gly Phe Tyr Pro Ser Asp
        370             375             380

Ile Ala Val Glu Trp Glu Ser Asn Gly Gln Pro Glu Asn Asn Tyr Lys
385             390             395             400

Thr Thr Pro Pro Val Leu Asp Ser Asp Gly Ser Phe Phe Leu Tyr Ser
                405             410             415

Arg Leu Thr Val Asp Lys Ser Arg Trp Gln Glu Gly Asn Val Phe Ser
            420             425             430

Cys Ser Val Leu His Glu Ala Leu His Asn His Tyr Thr Gln Lys Ser
        435             440             445

Leu Ser Leu Ser Leu Gly Gly Gly Gly Ser Ala Pro Thr Ser Ser
        450             455             460

Ser Thr Lys Lys Thr Gln Leu Gln Leu Glu His Leu Leu Leu Asp Leu
465             470             475             480

Gln Met Ile Leu Asn Gly Ile Asn Asn Tyr Lys Asn Pro Lys Leu Thr
                485             490             495

Ala Met Leu Thr Ala Lys Phe Ala Met Pro Lys Lys Ala Thr Glu Leu
            500             505             510
```

-continued

```
Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
        530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590
```

```
<210> SEQ ID NO 27
<211> LENGTH: 1851
<212> TYPE: DNA
<213> ORGANISM: Artificial Sequence
<220> FEATURE:
<223> OTHER INFORMATION: nucleotiedes coding fusion protein (GI102-M61)

<400> SEQUENCE: 27
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc      120 tgcggccaca acgtttcagt ggaagaactg gcccagacca ggatctactg gcagaaagaa      180
aagaaaatgg tgctgaccat gatgtccggc gacatgaaca tctggcctga gtacaagaac      240
cggaccatct tcgacatcac caacaacctg tccatcgtga ttctggccct gaggccttct      300
gatgagggca cctatgagtg cgtggtgctg aagtacgaga aggacgcctt caagcgcgag      360
cacctggctg aagtgacact gtccgtgaag gccgacttc ccacaccttc catctccgac      420
ttcgagatcc ctacctccaa catccggcgg atcatctgtt ctacctctgg cggctttcct      480
gagcctcacc tgtcttggct ggaaaacggc gaggaactga cgccatcaa caccaccgtg      540 tctcaggacc ccgaaaccga gctgtacgct gtgtcctcca agctggactt caacatgacc      600
accaaccaca gcttcatgtg cctgattaag tacggccacc tgagagtgaa ccagaccttc      660
aactggaaca ccaccaagca agagcacttc cctgacaatg atctggcgg cggaggttct      720 ggcggaggtg gaagcggagg cggaggatct gctgagtcta gtatggccc tccttgtcct      780 ccatgtcctg ctccagaagc tgctggcgga ccctctgtgt tcctgtttcc tccaaagcct      840
aaggaccagc tcatgatctc tcggacaccc gaagtgacct gcgtggtggt ggatgtgtct      900
caagaggacc ctgaggtgca gttcaattgg tacgtggacg gcgtggaagt gcacaacgcc      960
aagaccaagc ctagagagga cagttcaac tccacctaca gagtggtgtc cgtgctgacc     1020
gtgctgcacc aggattggct gaacggcaaa gagtacaagt gcaaggtgtc caacaagggc     1080
ctgccttcca gcatcgaaaa gaccatctcc aaggctaagg gccagcctag gaacccccag     1140
gtttacaccc tgcctccaag ccaagaggaa atgaccaaga ccaggtgtc cctgacctgc      1200 ctggtcaagg gcttctaccc ttccgacatt gccgtggaat gggagtccaa tggccagcct     1260
gagaacaact acaagaccac acctcctgtg ctggactccg acggctcctt ctttctgtac     1320
tctcgcctga ccgtggacaa gtctagatgg caagagggca acgtgttctc ctgctctgtg     1380
ctgcacgagg ccctgcacaa tcactacacc cagaagtccc tgtctctgtc tcttggaggt     1440
ggtggcggtt ctgcccctac cagctcctct accaagaaaa cccagctcca gttggagcat     1500
ctgctgctgg acctccagat gattctgaac gggatcaaca ctataagaa ccccaagctg      1560 accgccatgc tgaccgctaa gttctacatg cccaagaagg ccaccgagct gaagcacctc     1620
```

-continued cagtgcctgg aaagggaact gaagcccctg gaagaggtgc tgaatctggc ccagtccaag    1680
aacttccacc tgaggccacg ggacctgatc agcaacatca acgtgatcgt gctggaactg    1740
aagggctccg agacaacctt tatgtgcgag tacgccgacg agacagccac catcgtggaa    1800
tttctgaacc ggtggatcac cttctgccag agcatcatct ccacactgac c            1851

<210> SEQ ID NO 28
<211> LENGTH: 592
<212> TYPE: PRT
<213> ORGANISM: Artificial Sequence
<220> FEATURE:
<223> OTHER INFORMATION: fusion protein (GI102-M61)

<400> SEQUENCE: 28

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu

-continued

```
                325                330                335
Pro Ser Ser Ile Glu Lys Thr Ile Ser Lys Ala Lys Gly Gln Pro Arg
            340                345                350
Glu Pro Gln Val Tyr Thr Leu Pro Pro Ser Gln Glu Glu Met Thr Lys
            355                360                365
Asn Gln Val Ser Leu Thr Cys Leu Val Lys Gly Phe Tyr Pro Ser Asp
        370                375                380
Ile Ala Val Glu Trp Glu Ser Asn Gly Gln Pro Glu Asn Asn Tyr Lys
385                390                395                400
Thr Thr Pro Pro Val Leu Asp Ser Asp Gly Ser Phe Phe Leu Tyr Ser
                405                410                415
Arg Leu Thr Val Asp Lys Ser Arg Trp Gln Glu Gly Asn Val Phe Ser
            420                425                430
Cys Ser Val Leu His Glu Ala Leu His Asn His Tyr Thr Gln Lys Ser
            435                440                445
Leu Ser Leu Ser Leu Gly Gly Gly Gly Ser Ala Pro Thr Ser Ser
        450                455                460
Ser Thr Lys Lys Thr Gln Leu Gln Leu Glu His Leu Leu Leu Asp Leu
465                470                475                480
Gln Met Ile Leu Asn Gly Ile Asn Asn Tyr Lys Asn Pro Lys Leu Thr
                485                490                495
Ala Met Leu Thr Ala Lys Phe Tyr Met Pro Lys Lys Ala Thr Glu Leu
            500                505                510
Lys His Leu Gln Cys Leu Glu Arg Glu Leu Lys Pro Leu Glu Glu Val
            515                520                525
Leu Asn Leu Ala Gln Ser Lys Asn Phe His Leu Arg Pro Arg Asp Leu
        530                535                540
Ile Ser Asn Ile Asn Val Ile Val Leu Glu Leu Lys Gly Ser Glu Thr
545                550                555                560
Thr Phe Met Cys Glu Tyr Ala Asp Glu Thr Ala Thr Ile Val Glu Phe
                565                570                575
Leu Asn Arg Trp Ile Thr Phe Cys Gln Ser Ile Ile Ser Thr Leu Thr
            580                585                590
```

```
<210> SEQ ID NO 29
<211> LENGTH: 1857
<212> TYPE: DNA
<213> ORGANISM: Artificial Sequence
<220> FEATURE:
<223> OTHER INFORMATION: nucleotiedes coding fusion protein (GI102-M72)

<400> SEQUENCE: 29
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc     120 tgcggccaca cgtttcagt ggaagaactg gcccagacca ggatctactg cagaaagaa     180 aagaaaatgg tgctgaccat gatgtccggc gacatgaaca tctggcctga gtacaagaac     240
cggaccatct tcgacatcac caacaacctg tccatcgtga ttctggccct gaggccttct     300
gatgagggca cctatgagtg cgtggtgctg aagtacgaga aggacgcctt caagcgcgag     360
cacctggctg aagtgacact gtccgtgaag gccgactttc ccacaccttc catctccgac     420
ttcgagatcc ctacctccaa catccggcgg atcatctgtt ctacctctgg cggctttcct     480
gagcctcacc tgtcttggct ggaaaacggc gaggaactga cgccatcaa caccaccgtg     540 tctcaggacc ccgaaaccga gctgtacgct gtgtcctcca gctggactt caacatgacc     600
```

-continued

```
accaaccaca gcttcatgtg cctgattaag tacggccacc tgagagtgaa ccagaccttc      660
aactggaaca ccaccaagca agagcacttc cctgacaatg gatctggcgg cggaggttct      720
ggcggaggtg gaagcggagg cggaggatct gctgagtcta agtatggccc tccttgtcct      780
ccatgtcctg ctccagaagc tgctggcgga ccctctgtgt tcctgtttcc tccaaagcct      840
aaggaccagc tcatgatctc tcggacaccc gaagtgacct gcgtggtggt ggatgtgtct      900
caagaggacc ctgaggtgca gttcaattgg tacgtggacg gcgtggaagt gcacaacgcc      960
aagaccaagc ctagagagga acagttcaac tccacctaca gagtggtgtc cgtgctgacc      1020
gtgctgcacc aggattggct gaacggcaaa gagtacaagt gcaaggtgtc caacaagggc      1080 ctgcccttcca gcatcgaaaa gaccatctcc aaggctaagg ccagcctagg gaacccccag      1140
gtttacaccc tgcctccaag ccaagaggaa atgaccaaga accaggtgtc cctgacctgc      1200
ctggtcaagg gcttctaccc ttccgacatt gccgtggaat gggagtccaa tggccagcct      1260
gagaacaact acaagaccac acctcctgtg ctggactccg acggctcctt ctttctgtac      1320
tctcgcctga ccgtggacaa gtctagatgg caagagggca cgtgttctc ctgctctgtg       1380 ctgcacgagg ccctgcacaa tcactacacc cagaagtccc tgtctctgtc tcttggaggt      1440
ggtggcggtt ctgcccctac cagctcctct accaagaaaa cccagctcca gttggagcat      1500
ctgctgctgg acctccagat gattctgaac gggatcaaca ctataagaa ccccaagctg       1560 accgccatgc tgaccgctaa gttctacatg cccaagaagg ccaccgagct gaagcacctc      1620
cagtgcctgg aagaagaact gaagcccctg aagaggtgc tgaatggggc ccagtccaag       1680
aacttccacc tgaggccacg ggacctgatc agcaacatca cgtgatcgt gctggaactg       1740 aagggctccg agacaacctt tatgtgcgag tacgccgacg agacagccac catcgtggaa      1800
tttctgaacc ggtggatcac cttctgccag agcatcatct ccacactgac ctgatga        1857
```

<210> SEQ ID NO 30
<211> LENGTH: 592
<212> TYPE: PRT
<213> ORGANISM: Artificial Sequence
<220> FEATURE:
<223> OTHER INFORMATION: fusion protein (GI102-M72)

<400> SEQUENCE: 30

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140
```

```
Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
                180                 185                 190

Gln Thr Phe Asn Trp Asn Thr Thr Lys Gln Glu His Phe Pro Asp Asn
                195                 200                 205

Gly Ser Gly Gly Gly Gly Ser Gly Gly Gly Gly Ser Gly Gly Gly Gly
        210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
                260                 265                 270

Asp Val Ser Gln Glu Asp Pro Glu Val Gln Phe Asn Trp Tyr Val Asp
                275                 280                 285

Gly Val Glu Val His Asn Ala Lys Thr Lys Pro Arg Glu Glu Gln Phe
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
                340                 345                 350

Glu Pro Gln Val Tyr Thr Leu Pro Pro Ser Gln Glu Glu Met Thr Lys
                355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
                420                 425                 430

Cys Ser Val Leu His Glu Ala Leu His Asn His Tyr Thr Gln Lys Ser
                435                 440                 445

Leu Ser Leu Ser Leu Gly Gly Gly Gly Ser Ala Pro Thr Ser Ser
        450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
                500                 505                 510

Lys His Leu Gln Cys Leu Glu Glu Glu Leu Lys Pro Leu Glu Glu Val
                515                 520                 525

Leu Asn Gly Ala Gln Ser Lys Asn Phe His Leu Arg Pro Arg Asp Leu
        530                 535                 540

Ile Ser Asn Ile Asn Val Ile Val Leu Glu Leu Lys Gly Ser Glu Thr
545                 550                 555                 560
```

```
Thr Phe Met Cys Glu Tyr Ala Asp Glu Thr Ala Thr Ile Val Glu Phe
            565                 570                 575

Leu Asn Arg Trp Ile Thr Phe Cys Gln Ser Ile Ile Ser Thr Leu Thr
            580                 585                 590
```

```
<210> SEQ ID NO 31
<211> LENGTH: 1851
<212> TYPE: DNA
<213> ORGANISM: Artificial Sequence
<220> FEATURE:
<223> OTHER INFORMATION: nucleotiedes coding fusion protein (GI101w)

<400> SEQUENCE: 31
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc      120 tgcggccaca acgtttcagt ggaagaactg gcccagacca ggatctactg gcagaaagaa      180
aagaaaatgg tgctgaccat gatgtccggc gacatgaaca tctggcctga gtacaagaac      240
cggaccatct tcgacatcac caacaacctg tccatcgtga ttctggccct gaggccttct      300
gatgagggca cctatgagtg cgtggtgctg aagtacgaga aggacgcctt caagcgcgag      360
cacctggctg aagtgacact gtccgtgaag gccgactttc ccacaccttc catctccgac      420
ttcgagatcc ctacctccaa catccggcgg atcatctgtt ctacctctgg cggctttcct      480
gagcctcacc tgtcttggct ggaaaacggc gaggaactga cgccatcaa caccaccgtg      540 tctcaggacc ccgaaaccga gctgtacgct gtgtcctcca agctggactt caacatgacc      600
accaaccaca gcttcatgtg cctgattaag tacggccacc tgagagtgaa ccagaccttc      660
aactggaaca ccaccaagca agagcacttc cctgacaatg gatctggcgg cggaggttct      720
ggcggaggtg gaagcggagg cggaggatct gctgagtcta gtatggccc tccttgtcct      780 ccatgtcctg ctccagaagc tgctggcgga ccctctgtgt tcctgtttcc tccaaagcct      840
aaggaccagc tcatgatctc tcggacaccc gaagtgacct gcgtggtggt ggatgtgtct      900
caagaggacc ctgaggtgca gttcaattgg tacgtggacg gcgtggaagt gcacaacgcc      960
aagaccaagc ctagagagga acagttcaac tccacctaca gagtggtgtc cgtgctgacc      1020
gtgctgcacc aggattggct gaacggcaaa gagtacaagt gcaaggtgtc caacaagggc      1080
ctgccttcca gcatcgaaaa gaccatctcc aaggctaagg gccagcctag gaaccccag      1140 gtttacaccc tgcctccaag ccaagaggaa atgaccaaga ccaggtgtc cctgacctgc      1200 ctggtcaagg gcttctaccc ttccgacatt gccgtggaat gggagtccaa tggccagcct      1260
gagaacaact acaagaccac acctcctgtg ctggactccg acggctcctt ctttctgtac      1320
tctcgcctga ccgtggacaa gtctagatgg caagagggca cgtgttctc ctgctctgtg      1380 ctgcacgagg ccctgcacaa tcactacacc cagaagtccc tgtctctgtc tcttggaggt      1440
ggtggcggtt ctgcccctac cagctcctct accaagaaaa cccagctcca gttggagcat      1500
ctgctgctgg acctccagat gattctgaac gggatcaaca ctataagaa ccccaagctg      1560 acccgcatgc tgaccttaa gttctacatg cccaagaagg ccaccgagct gaagcacctc      1620
cagtgcctgg aagaagaact gaagcccctg aagaggtgc tgaatctggc ccagtccaag      1680
aacttccacc tgaggccacg ggacctgatc agcaacatca cgtgatcgt gctggaactg      1740 aagggctccg agacaacctt tatgtgcgag tacgccgacg agacagccac catcgtggaa      1800
tttctgaacc ggtggatcac cttctgccag agcatcatct ccacactgac c            1851
```

```
<210> SEQ ID NO 32
<211> LENGTH: 592
<212> TYPE: PRT
<213> ORGANISM: Artificial Sequence
<220> FEATURE:
<223> OTHER INFORMATION: fusion protein (GI101w)

<400> SEQUENCE: 32

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
```

-continued

```
        370             375             380

Ile Ala Val Glu Trp Glu Ser Asn Gly Gln Pro Glu Asn Asn Tyr Lys
385             390             395             400

Thr Thr Pro Pro Val Leu Asp Ser Asp Gly Ser Phe Phe Leu Tyr Ser
            405             410             415

Arg Leu Thr Val Asp Lys Ser Arg Trp Gln Glu Gly Asn Val Phe Ser
            420             425             430

Cys Ser Val Leu His Glu Ala Leu His Asn His Tyr Thr Gln Lys Ser
        435             440             445

Leu Ser Leu Ser Leu Gly Gly Gly Gly Ser Ala Pro Thr Ser Ser
        450             455             460

Ser Thr Lys Lys Thr Gln Leu Gln Leu Glu His Leu Leu Leu Asp Leu
465             470             475             480

Gln Met Ile Leu Asn Gly Ile Asn Asn Tyr Lys Asn Pro Lys Leu Thr
            485             490             495

Arg Met Leu Thr Phe Lys Phe Tyr Met Pro Lys Lys Ala Thr Glu Leu
            500             505             510

Lys His Leu Gln Cys Leu Glu Glu Glu Leu Lys Pro Leu Glu Glu Val
        515             520             525

Leu Asn Leu Ala Gln Ser Lys Asn Phe His Leu Arg Pro Arg Asp Leu
        530             535             540

Ile Ser Asn Ile Asn Val Ile Val Leu Glu Leu Lys Gly Ser Glu Thr
545             550             555             560

Thr Phe Met Cys Glu Tyr Ala Asp Glu Thr Ala Thr Ile Val Glu Phe
            565             570             575

Leu Asn Arg Trp Ile Thr Phe Cys Gln Ser Ile Ile Ser Thr Leu Thr
            580             585             590
```

<210> SEQ ID NO 33
<211> LENGTH: 1848
<212> TYPE: DNA
<213> ORGANISM: Artificial Sequence
<220> FEATURE:
<223> OTHER INFORMATION: nucleotiedes coding fusion protein (mGI102-M61)

<400> SEQUENCE: 33

```
atggatgcta tgctgagagg cctgtgttgc gtgctgctgc tgtgtggcgc tgtgttcgtg    60
tctccttctc acgctgtgga cgagcagctc tccaagtccg tgaaggataa ggtcctgctg   120
ccttgccggt acaactctcc tcacgaggac gagtctgagg accggatcta ctggcagaaa   180
cacgacaagg tggtgctgtc cgtgatcgcc ggaaagctga agtgtggcc tgagtacaag   240 aacaggaccc tgtacgacaa caccacctac agcctgatca tcctgggcct cgtgctgagc   300
gatagaggca cctattcttg cgtggtgcag aagaaagagc ggggcaccta cgaagtgaag   360
cacctggctc tggtcaagct gtccatcaag gccgacttca gcacccctaa catcaccgag   420
tctggcaacc cttccgccga caccaagaga atcacctgtt cgcctctgg cggcttccct   480 aagcctcggt tctcttggct ggaaaacggc agagagctgc ccggcatcaa taccaccatt   540
tctcaggacc cagagtccga gctgtacacc atctccagcc agctcgactt taacaccacc   600
agaaaccaca ccatcaagtg cctgattaag tacggcgacg cccacgtgtc cgaggacttt   660
acttgggaga aacctcctga ggaccctcct gactctggat ctggcggcgg aggttctggc   720
ggaggtggaa gcgaggcgg aggatctgct gagtctaagt atggccctcc ttgtcctcca   780
tgtcctgctc agaagctgc tggcggaccc tctgtgttcc tgtttcctcc aaagcctaag   840
```

```
gaccagctca tgatctctcg gacccctgaa gtgacctgcg tggtggtgga tgtgtctcaa      900
gaggaccctg aggtgcagtt caattggtac gtggacggcg tggaagtgca caacgccaag      960
accaagccta gagaggaaca gttcaactcc acctatagag tggtgtccgt gctgaccgtg     1020
ctgcaccagg attggctgaa cggcaaagag tacaagtgca aggtgtccaa caagggcctg     1080
ccttccagca tcgaaaagac catcagcaag gctaagggcc agcctaggga accccaggtt     1140
tacaccctgc ctccaagcca agaggaaatg accaagaacc aggtgtccct gacctgcctg     1200
gtcaagggct tctacccttc cgacattgcc gtggaatggg agtccaatgg ccagcctgag     1260
aacaactaca agaccacacc tcctgtgctg gactccgacg gctccttctt tctgtactct     1320
cgcctgaccg tggacaagtc taggtggcaa gagggcaacg tgttctcctg ctctgtgctg     1380
cacgaggctc tgcacaacca ctacacccag aagtccctgt ctctgtctct tggaggtggt     1440
ggcggttctg cccctacctc cagctctacc aagaaaaccc agctccagtt ggagcatctg     1500
ctgctggacc tccagatgat cctgaatggc atcaacaatt acaagaaccc caagctgacc     1560
gccatgctga ccgctaagtt ctacatgccc aagaaggcca ccgagctgaa gcacttgcag     1620
tgcctggaaa gggaactgaa gcccctggaa gaagtgctga atctggccca gtccaagaac     1680
ttccacctga ggcctaggga cctgatctcc aacatcaacg tgatcgtgct ggaactgaaa     1740
ggctccgaga caaccttcat gtgcgagtac gccgacgaga cagccaccat cgtggaattt     1800
ctgaaccggt ggatcacctt ctgccagagc atcatctcca cactgacc                  1848
```

```
<210> SEQ ID NO 34
<211> LENGTH: 616
<212> TYPE: PRT
<213> ORGANISM: Artificial Sequence
<220> FEATURE:
<223> OTHER INFORMATION: fusion protein (mGI102-M61)

<400> SEQUENCE: 34

Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190
```

-continued

```
Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220

Pro Pro Glu Asp Pro Pro Asp Ser Gly Ser Gly Gly Gly Ser Gly
225                 230                 235                 240

Gly Gly Gly Ser Gly Gly Gly Ser Ala Glu Ser Lys Tyr Gly Pro
                245                 250                 255

Pro Cys Pro Pro Cys Pro Ala Pro Glu Ala Ala Gly Gly Pro Ser Val
                260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
        290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
                340                 345                 350

Cys Lys Val Ser Asn Lys Gly Leu Pro Ser Ser Ile Glu Lys Thr Ile
                355                 360                 365

Ser Lys Ala Lys Gly Gln Pro Arg Glu Pro Gln Val Tyr Thr Leu Pro
        370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
                420                 425                 430

Asp Gly Ser Phe Phe Leu Tyr Ser Arg Leu Thr Val Asp Lys Ser Arg
                435                 440                 445

Trp Gln Glu Gly Asn Val Phe Ser Cys Ser Val Leu His Glu Ala Leu
        450                 455                 460

His Asn His Tyr Thr Gln Lys Ser Leu Ser Leu Ser Leu Gly Gly Gly
465                 470                 475                 480

Gly Gly Ser Ala Pro Thr Ser Ser Ser Thr Lys Lys Thr Gln Leu Gln
                485                 490                 495

Leu Glu His Leu Leu Leu Asp Leu Gln Met Ile Leu Asn Gly Ile Asn
        500                 505                 510

Asn Tyr Lys Asn Pro Lys Leu Thr Ala Met Leu Thr Ala Lys Phe Tyr
        515                 520                 525

Met Pro Lys Lys Ala Thr Glu Leu Lys His Leu Gln Cys Leu Glu Arg
    530                 535                 540

Glu Leu Lys Pro Leu Glu Glu Val Leu Asn Leu Ala Gln Ser Lys Asn
545                 550                 555                 560

Phe His Leu Arg Pro Arg Asp Leu Ile Ser Asn Ile Asn Val Ile Val
                565                 570                 575

Leu Glu Leu Lys Gly Ser Glu Thr Thr Phe Met Cys Glu Tyr Ala Asp
                580                 585                 590

Glu Thr Ala Thr Ile Val Glu Phe Leu Asn Arg Trp Ile Thr Phe Cys
        595                 600                 605
```

```
Gln Ser Ile Ile Ser Thr Leu Thr
    610             615

<210> SEQ ID NO 35
<211> LENGTH: 153
<212> TYPE: PRT
<213> ORGANISM: Artificial Sequence
<220> FEATURE:
<223> OTHER INFORMATION: wild type hIL-2

<400> SEQUENCE: 35

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 36
<211> LENGTH: 158
<212> TYPE: PRT
<213> ORGANISM: Artificial Sequence
<220> FEATURE:
<223> OTHER INFORMATION: IL-2 with signal sequence

<400> SEQUENCE: 36

Met Asp Ala Met Leu Arg Gly Leu Cys Cys Val Leu Leu Leu Cys Gly
1               5                   10                  15

Ala Val Phe Val Ser Pro Ser His Ala Ala Pro Thr Ser Ser Ser Thr
            20                  25                  30

Lys Lys Thr Gln Leu Gln Leu Glu His Leu Leu Leu Asp Leu Gln Met
        35                  40                  45

Ile Leu Asn Gly Ile Asn Asn Tyr Lys Asn Pro Lys Leu Thr Arg Met
    50                  55                  60

Leu Thr Phe Lys Phe Tyr Met Pro Lys Lys Ala Thr Glu Leu Lys His
65                  70                  75                  80

Leu Gln Cys Leu Glu Glu Glu Leu Lys Pro Leu Glu Glu Val Leu Asn
                85                  90                  95

Leu Ala Gln Ser Lys Asn Phe His Leu Arg Pro Arg Asp Leu Ile Ser
            100                 105                 110

Asn Ile Asn Val Ile Val Leu Glu Leu Lys Gly Ser Glu Thr Thr Phe
        115                 120                 125

Met Cys Glu Tyr Ala Asp Glu Thr Ala Thr Ile Val Glu Phe Leu Asn
    130                 135                 140
```

```
Arg Trp Ile Thr Phe Cys Gln Ser Ile Ile Ser Thr Leu Thr
145                 150                 155
```

<210> SEQ ID NO 37
<211> LENGTH: 474
<212> TYPE: DNA
<213> ORGANISM: Artificial Sequence
<220> FEATURE:
<223> OTHER INFORMATION: nucleotide sequence coding IL-2 with signal
      sequence

<400> SEQUENCE: 37

```
atggatgcta tgctgagagg cctgtgttgc gtgctgctgc tgtgtggcgc tgtgttcgtg     60
tctccttctc acgctgcccc taccagctcc tctaccaaga aaacccagct ccagttggag    120
catctgctgc tggacctcca gatgattctg aacgggatca acaactataa gaaccccaag    180
ctgacccgca tgctgacctt taagttctac atgcccaaga aggccaccga gctgaagcac    240
ctccagtgcc tggaagaaga actgaagccc ctggaagagg tgctgaatct ggcccagtcc    300
aagaacttcc acctgaggcc acgggacctg atcagcaaca tcaacgtgat cgtgctggaa    360
ctgaagggct ccgagacaac ctttatgtgc gagtacgccg acgagacagc caccatcgtg    420
gaatttctga accggtggat caccttctgc cagagcatca tctccacact gacc         474
```

<210> SEQ ID NO 38
<211> LENGTH: 591
<212> TYPE: PRT
<213> ORGANISM: Artificial Sequence
<220> FEATURE:
<223> OTHER INFORMATION: mGI-101

<400> SEQUENCE: 38

```
Val Asp Glu Gln Leu Ser Lys Ser Val Lys Asp Lys Val Leu Leu Pro
1               5                   10                  15

Cys Arg Tyr Asn Ser Pro His Glu Asp Glu Ser Glu Asp Arg Ile Tyr
                20                  25                  30

Trp Gln Lys His Asp Lys Val Val Leu Ser Val Ile Ala Gly Lys Leu
            35                  40                  45

Lys Val Trp Pro Glu Tyr Lys Asn Arg Thr Leu Tyr Asp Asn Thr Thr
        50                  55                  60

Tyr Ser Leu Ile Ile Leu Gly Leu Val Leu Ser Asp Arg Gly Thr Tyr
65                  70                  75                  80

Ser Cys Val Val Gln Lys Lys Glu Arg Gly Thr Tyr Glu Val Lys His
                85                  90                  95

Leu Ala Leu Val Lys Leu Ser Ile Lys Ala Asp Phe Ser Thr Pro Asn
                100                 105                 110

Ile Thr Glu Ser Gly Asn Pro Ser Ala Asp Thr Lys Arg Ile Thr Cys
            115                 120                 125

Phe Ala Ser Gly Gly Phe Pro Lys Pro Arg Phe Ser Trp Leu Glu Asn
        130                 135                 140

Gly Arg Glu Leu Pro Gly Ile Asn Thr Thr Ile Ser Gln Asp Pro Glu
145                 150                 155                 160

Ser Glu Leu Tyr Thr Ile Ser Ser Gln Leu Asp Phe Asn Thr Thr Arg
                165                 170                 175

Asn His Thr Ile Lys Cys Leu Ile Lys Tyr Gly Asp Ala His Val Ser
                180                 185                 190

Glu Asp Phe Thr Trp Glu Lys Pro Pro Glu Asp Pro Pro Asp Ser Gly
            195                 200                 205
```

Ser Gly Gly Gly Gly Ser Gly Gly Gly Gly Ser Gly Gly Gly Gly Ser
210             215             220

Ala Glu Ser Lys Tyr Gly Pro Pro Cys Pro Pro Cys Pro Ala Pro Glu
225             230             235             240

Ala Ala Gly Gly Pro Ser Val Phe Leu Phe Pro Pro Lys Pro Lys Asp
245             250             255

Gln Leu Met Ile Ser Arg Thr Pro Glu Val Thr Cys Val Val Val Asp
260             265             270

Val Ser Gln Glu Asp Pro Glu Val Gln Phe Asn Trp Tyr Val Asp Gly
275             280             285

Val Glu Val His Asn Ala Lys Thr Lys Pro Arg Glu Glu Gln Phe Asn
290             295             300

Ser Thr Tyr Arg Val Val Ser Val Leu Thr Val Leu His Gln Asp Trp
305             310             315             320

Leu Asn Gly Lys Glu Tyr Lys Cys Lys Val Ser Asn Lys Gly Leu Pro
325             330             335

Ser Ser Ile Glu Lys Thr Ile Ser Lys Ala Lys Gly Gln Pro Arg Glu
340             345             350

Pro Gln Val Tyr Thr Leu Pro Pro Ser Gln Glu Glu Met Thr Lys Asn
355             360             365

Gln Val Ser Leu Thr Cys Leu Val Lys Gly Phe Tyr Pro Ser Asp Ile
370             375             380

Ala Val Glu Trp Glu Ser Asn Gly Gln Pro Glu Asn Asn Tyr Lys Thr
385             390             395             400

Thr Pro Pro Val Leu Asp Ser Asp Gly Ser Phe Phe Leu Tyr Ser Arg
405             410             415

Leu Thr Val Asp Lys Ser Arg Trp Gln Glu Gly Asn Val Phe Ser Cys
420             425             430

Ser Val Leu His Glu Ala Leu His Asn His Tyr Thr Gln Lys Ser Leu
435             440             445

Ser Leu Ser Leu Gly Gly Gly Gly Gly Ser Ala Pro Thr Ser Ser Ser
450             455             460

Thr Lys Lys Thr Gln Leu Gln Leu Glu His Leu Leu Leu Asp Leu Gln
465             470             475             480

Met Ile Leu Asn Gly Ile Asn Asn Tyr Lys Asn Pro Lys Leu Thr Ala
485             490             495

Met Leu Thr Ala Lys Phe Tyr Met Pro Lys Lys Ala Thr Glu Leu Lys
500             505             510

His Leu Gln Cys Leu Glu Glu Glu Leu Lys Pro Leu Glu Glu Val Leu
515             520             525

Asn Leu Ala Gln Ser Lys Asn Phe His Leu Arg Pro Arg Asp Leu Ile
530             535             540

Ser Asn Ile Asn Val Ile Val Leu Glu Leu Lys Gly Ser Glu Thr Thr
545             550             555             560

Phe Met Cys Glu Tyr Ala Asp Glu Thr Ala Thr Ile Val Glu Phe Leu
565             570             575

Asn Arg Trp Ile Thr Phe Cys Gln Ser Ile Ile Ser Thr Leu Thr
580             585             590